US010441677B2

(12) United States Patent
White et al.

(10) Patent No.: US 10,441,677 B2
(45) Date of Patent: Oct. 15, 2019

(54) METHODS AND COMPOSITIONS FOR TREATING TENDON DEGENERATION

(71) Applicant: Anika Therapeutics, Inc., Bedford, MA (US)

(72) Inventors: Colin D. White, Lynnfield, MA (US); Edward S. Ahn, Dover, MA (US); Sekoni Daouda Noel, Newton Centre, MA (US)

(73) Assignee: Anika Therapeutics, Inc., Bedford, MA (US)

( * ) Notice: Subject to any disclaimer, the term of this patent is extended or adjusted under 35 U.S.C. 154(b) by 0 days.

(21) Appl. No.: 15/497,577

(22) Filed: Apr. 26, 2017

(65) Prior Publication Data

US 2017/0326271 A1   Nov. 16, 2017

Related U.S. Application Data

(60) Provisional application No. 62/367,377, filed on Jul. 27, 2016, provisional application No. 62/328,396, filed on Apr. 27, 2016.

(51) Int. Cl.
| A61L 27/20 | (2006.01) |
| A61L 27/38 | (2006.01) |
| A61L 27/50 | (2006.01) |
| A61K 31/715 | (2006.01) |

(52) U.S. Cl.
CPC ............ A61L 27/20 (2013.01); A61K 31/715 (2013.01); A61L 27/386 (2013.01); A61L 27/50 (2013.01); A61L 2400/06 (2013.01); A61L 2430/10 (2013.01)

(58) Field of Classification Search
CPC ........ A61L 27/20; A61L 27/50; A61L 27/386; A61L 2430/10; A61L 2400/06
USPC ......................................................... 514/54
See application file for complete search history.

(56) References Cited

U.S. PATENT DOCUMENTS

| 2,946,819 | A | 7/1960 | Coles |
| 3,231,610 | A | 1/1966 | Engelbert |
| 3,502,722 | A | 3/1970 | Neumann |
| 3,644,456 | A | 2/1972 | Ulrich |
| 3,972,933 | A | 8/1976 | Lawton |
| 4,014,935 | A | 3/1977 | Ibbotson |
| 4,066,629 | A | 1/1978 | Edelman |
| 4,085,140 | A | 4/1978 | Ibbotson |
| 4,096,334 | A | 6/1978 | Keil |
| 4,137,386 | A | 1/1979 | Smith |
| 4,851,521 | A | 7/1989 | della Valle et al. |
| 5,356,883 | A | 10/1994 | Kuo et al. |
| 5,676,964 | A | 10/1997 | Della Valle et al. |
| 6,013,679 | A | 1/2000 | Kuo et al. |
| 6,027,741 | A | 2/2000 | Cialdi et al. |
| 6,537,979 | B1 | 3/2003 | Kuo et al. |
| 6,548,081 | B2 | 4/2003 | Sadozai et al. |
| 6,579,978 | B1 | 6/2003 | Renier et al. |
| 6,620,927 | B2 | 9/2003 | Bulpitt et al. |
| 7,125,860 | B1 | 10/2006 | Renier et al. |
| 7,462,606 | B2 | 12/2008 | Bellini et al. |
| 7,683,038 | B2 | 3/2010 | Bellini et al. |
| 7,884,087 | B1 | 2/2011 | Bellini et al. |
| 8,053,423 | B2 | 11/2011 | Lamberti et al. |
| 8,124,120 | B2 | 2/2012 | Sadozai et al. |
| 8,178,499 | B2 | 5/2012 | Bellini et al. |
| 8,178,663 | B2 | 5/2012 | Bellini et al. |
| 8,323,617 | B2 | 12/2012 | Gooding et al. |
| 2005/0080037 | A1 | 4/2005 | Petrella |
| 2006/0134421 | A1 | 6/2006 | Zeiringer et al. |
| 2006/0272221 | A1 | 12/2006 | Dazza et al. |
| 2012/0010280 | A1 | 1/2012 | Aleo et al. |
| 2012/0316513 | A1 | 12/2012 | Sharkey et al. |
| 2015/0045887 | A1 | 2/2015 | Mathies |

FOREIGN PATENT DOCUMENTS

| CA | 2 541 813 | 4/2005 |
| CN | 1859918 A | 11/2006 |
| EP | 0216453 B1 | 4/1987 |
| EP | 1095064 B1 | 5/2001 |
| EP | 1237585 B1 | 9/2002 |
| EP | 1891984 A1 | 2/2008 |
| ES | 2317018 T3 | 4/2009 |
| WO | WO-0001733 A1 | 1/2000 |
| WO | WO-2004000374 A1 | 12/2003 |
| WO | WO-2005032562 A1 | 4/2005 |
| WO | WO-2005034965 A1 | 4/2005 |
| WO | WO-2008157767 A1 | 12/2008 |
| WO | WO-2013139955 A1 | 9/2013 |
| WO | WO-2014049063 A1 | 4/2014 |
| WO | WO-2015123778 A1 | 8/2015 |

OTHER PUBLICATIONS

Glossary of medical education terms, Institute of International Medical Education. http://www.iime.org/glossary.htm Accessed in Mar. 2013. (Year: 2013).*
Pereira et al. Chapter 6 Hyaluronic Acid. Advances in Experimental Medicine and Biology 1059, J. M. Oliveira et al. (eds.), Osteochondral Tissue Engineering, Springer International Publishing AG, part of Springer Nature 2018. https://doi.org/10.1007/978-3-319-76735-2_6 (Year: 2018).*
Abrams, et al., "Subchondral Bone Treatment," in *Biologic Knee Reconstruction: A Surgeon's Guide*, Cole BJ, Harris JD, eds.; Ch. 12, pp. 83-89 (2015) (7 pages).
Ahmadzadeh-Asl, S., et al., "Preparation and characterisation of calcium phosphate-hyaluronic acid nanocomposite bone cement", Advances in Applied Ceramics: Structural, Functional and Bioceramics, 110:6, 340-345, Aug. 1, 2011 (7 pages).

(Continued)

*Primary Examiner* — Yih-Horng Shiao
(74) *Attorney, Agent, or Firm* — Wolf, Greenfield & Sacks, P.C.

(57) ABSTRACT

Injectable compositions and methods for treating an injured tendon in an animal or human are disclosed herein. The injectable compositions include an effective amount of a carbohydrate to increase osteotendinous hydration and lubrication.

24 Claims, 7 Drawing Sheets

(56) References Cited

OTHER PUBLICATIONS

Anika Therapeutics, Inc., "Study of Sodium Hyaluronate to Provide Symptomatic Relief of Lateral Epicondylosis (Tennis Elbow)," ClinicalTrials.gov identifier: NCT02861183; Downloaded from https://clinicaltrials.gov/ct2/show/NCT02861183 on Aug. 17, 2016 (4 pgs.).

Benjamin, M. et al, "Microdamage and Altered Vascularity at the Enthesis-Bone Interface Provides an Anatomic Explanation for Bone Involvement in the HLA-B27-Associated Spondylarthritides and Allied Disorders", Arthritis & Rheumatism, 56(1):224-233, Jan. 2007 (10 pages).

Benjamin, M. et al., "Where tendons and ligaments meet bone: attachment sites ('entheses') in relation to exercise and/or mechanical load", J. Anat., 208:471-490, 2006 (20 pages).

Dourte, L. et al., "Tendon Properties Remain Altered in a Chronic Rat Rotator Cuff Model", Clin. Orthop. Relat. Res., 468:1485-1492, Jun. 2010 (8 pages).

Gorelick, L. et al., "Lateral Epicondylitis Injection Therapy: A Safety and Efficacy Analysis of Hyaluronate versus Corticosteroid Injections," Adv. Tech. Biol. Med., vol. 3, No. 2, (2015) (4 pages).

International Search Report and Written Opinion issued by the European Patent Office as International Searching Authority in PCT/US2017/029635, dated Sep. 5, 2017 (23 pages).

Kannus, P., "Structure of the tendon connective tissue", Scand J Med Sci Sports, 10:312-320, 2000 (9 pages).

Kolodzinskyi, M. et al., "The Effects of Hylan G-F 20 Surface Modification on Gliding of Extrasynovial Canine Tendon Grafts In Vitro," J. Hand Surg. Am., vol. 38A, pp. 231-236, Feb. 2013 (6 pages).

Kraushaar, B. et al., "Current Concepts Review Tendinosis of the Elbow (Tennis Elbow): Clinical Features and Findings of Histological, Immunohistochemical, and Electron Microscopy Studies", The Journal of Bone and Joint Surgery, Incorporated, 81-A(2):259-278, Feb. 1999 (20 pages).

Li, et al., "Subchondral bone in osteoarthritis: insight into risk factors and microstructural changes," Arthritis Research & Therapy, vol. 15, (2013) (12 pages).

Yoshida, M., et al., "Therapeutic effects of high molecular weight hyaluronan injections for tendinopathy in a rat model", Journal of Orthop Sci, 20(1):186-195, Sep. 25, 2014 (10 pages).

Nishida, J. et al., "Effect of hyaluronic acid on the excursion resistance of tendon grafts" Journal of Bone & Joint Surgery (Br.), 86-6:918-924, Aug. 2004 (7 pages).

Petrella, R.J. et al., "Management of Tennis Elbow with sodium hyaluronate periarticular injections", Sports Medicine, Arthroscopy, Rehabilitation, Therapy & Technology, vol. 2, No. 4 (2010) (6 pages).

Sharma, P. et al., "Tendon Injury and Tendinopahty: Healing and Repair", Journal of Bone & Joint Surgery,87:187-202, Jan. 2005 (17 pages).

Yu, Y. et al., "Ras/Raf/MEK/ERK Pathway Is Associated with Lung Metastasis of Osteosarcoma in an Orthotopic Mouse Model", Anticancer Research, vol. 31: 1147-1152 (2011) (6 pages).

Best, et al., "Chapter 4: Skeletal Muscle and Tendon" in *Practical Orthopaedic Sports Medicine and Arthroscopy*, Johnson and Pedowitz Eds., Wolters Kluwer Health, Philadelphia, Pennsylvania, pp. 37-50, 2007 (20 pages).

Ho, et al., "Chapter 9: Tendon Injuries", In *Essentials in Elbow Surgery*, Antuna and Barco Eds., Springer-Verlag, London, pp. 141-159, 2014 (21 pages).

Renstrom, et al., "Chapter 9: Insertional Tendinopathy in Sports", in *Tendon Injuries: Basic Science and Clinical Medicine*, Maffulli, et al., Eds., Springer-Verlag, London, pp. 70-85, 2005 (19 pages).

Walsh, et al., "Chapter 67: Injection Procedures", in *DeLisa's Physical Medicine & Rehabilitation: Principles and Practice*, vol. 1, Fifth Edition, Frontera, et al., Eds., Wolters Kluwer, Philadelphia, Pennsylvania, pp. 1815-1873, 2010 (64 pages).

Wu, et al., "Tendon injuries: basic science and new repair proposals", EFORT Open Reviews, 2:332-342, Jul. 2017 (11 pages).

International Preliminary Report on Patentability for Application No. PCT/US2017/029635 dated Nov. 8, 2018.

Jose et al., A Comparative Study on the Efficacy of Local Infiltration of Autologous Blood versus Local Corticosteroid Infiltration for the Treatment of Chronic Lateral Epicondylitis Elbow. IOSR Journal of Dental and Medical Sciences. Jul. 2016;15(6):49-53.

Kjaer et al., From mechanical loading to collagen synthesis, structural changes and function in human tendon. Scand J Med Sci Sports. Aug. 2009;19(4):500-10. doi: 10.1111/j.1600-0838.2009.00986.x.

Langberg et al., Eccentric rehabilitation exercise increases peritendinous type I collagen synthesis in humans with Achilles tendinosis. Scand J Med Sci Sports. Feb. 2007;17(1):61-6. Epub Jun. 19, 2006.

Osti et al., Hyaluronic acid increases tendon derived cell viability and collagen type I expression in vitro: Comparative study of four different Hyaluronic acid preparations by molecular weight. BMC Musculoskelet Disord. Oct. 6, 2015;16:284. doi: 10.1186/s12891-0150735-7.

Paoloni et al., Topical nitric oxide application in the treatment of chronic extensor tendinosis at the elbow: a randomized, double-blinded, placebo-controlled clinical trial. Am J Sports Med. Nov.-Dec. 2003;31(6):915-20.

Sims et al., Non-surgical treatment of lateral epicondylitis: a systematic review of randomized controlled trials. Hand (N Y). Dec. 2014;9(4):419-46. doi: 10.1007/s11552-014-9642-x.

Walrod et al., Lateral Epicondylitis Treatment & Management: Treatment Options, Acute Phase, Recovery Phase. Medscape. Oct. 30, 2018:1-18. Retrieved from the Internet: https://emedicine.medscape.com/article/996969-treatment on Jul. 18, 2019.

Young, Novel Collagen Scores Well in Tendinopathy Test. Orthopedics—This Week. Feb. 15, 2016. Retrieved from the Internet: http://ryortho.com/breaking/novel-collagen-scores-well-in-tendinopathy-test/ on Jul. 18, 2019. 2 pages.

PCT/US2017/029635, Nov. 8, 2018, International Preliminary Report on Patentability.

* cited by examiner

METHODS AND COMPOSITIONS FOR TREATING TENDON DEGENERATION

CROSS REFERENCE TO RELATED APPLICATIONS

This application claims the benefit of priority of U.S. Provisional Application No. 62/328,396, filed Apr. 27, 2016 and U.S. Provisional Application No. 62/367,377, filed Jul. 27, 2016, the contents of each of which are hereby incorporated by reference.

FIELD OF THE INVENTION

The present disclosure relates to methods and injectable compositions for treating tendon degeneration. In particular, the present disclosure provides injectable compositions comprising a carbohydrate for treating an injured tendon in an animal or human by increasing hydration and lubrication of a degenerate osteotendinous junction at any joint, particularly when the composition is administered via intra-osteotendinous or peri-osteotendinous injection. Furthermore, the present disclosure also relates to methods of using the disclosed compositions to treat an injured tendon in a subject.

BACKGROUND

Tendinopathy is a common clinical disorder. The most common tendinopathy, lateral epicondylitis (tennis elbow) affects up to 3% of the general population. It can be responsible for substantial pain and loss of function of the affected limb for over one year in up to 20% of people. Current management protocols include conservative therapy, e.g., bracing and physiotherapy (66.5% of patients); corticosteroid injections (26% of patients); or surgical resection of the damaged portion of the tendon (7.5% of patients) with patients progressing to the next stage of treatment when their symptoms become too extreme to tolerate. Physicians typically agree that the short-term effects of corticosteroids are outweighed by the longer term consequences of their overuse in this condition. Other common tendinopathies include shoulder (rotator cuff tendinopathy) that affects 1.1% of the population annually, ankle (Achilles tendinopathy), knee (patellar tendinopathy), as well as tendinopathies of the other tendons referenced in Table 1.

Tendinopathy

Tendinopathy is said to be a degenerative condition affecting a tendon. The cause of this degeneration has been thought to be due to one of several causes, of which overuse causing micro-trauma at the tendon enthesis appears to be the most widely accepted. However, practitioners have treated the enthesis as a single unit and have not been cognizant of the biomechanical variation within the enthesis. Instead of targeting an appropriate location within the enthesis in need of treatment, practitioners will treat the entire unit, resulting in inconsistent clinical outcomes. The present invention focuses on the treatment of the osteotendinous junction and not the tendon or musculotendinous junctions.

Histological findings suggest that chronic tendon injuries at the osteotendinous junction are degenerative in nature and not inflammatory. There is an absence of inflammatory cells (e.g., macrophages, neutrophils, monocytes) suggesting that corticosteroid treatment will be of limited benefit in tendinopathy. There is therefore no consensus treatment for tendinopathy (e.g., tennis elbow) within the medical community. As stated previously, this lack of consensus may be because the medical community is viewing the tendon enthesis as a single unit instead of segmenting the regions amenable to treatment. While traditional treatments for tendinopathy have involved the use of corticosteroid injections for pain reduction, it has been shown that corticosteroid injections can further the degeneration of tendons and increase the risk of recurrence of the condition as well as increase the risk of tendon rupture. Nonetheless, corticosteroid injections have been shown to be effective in short term pain reduction for tendinopathy in certain instances. The mechanism is unclear but it is thought that bathing the area with the steroid composition may alter or interfere with the local chemicals that cause the pain stimulus in the area.

Other treatments for tendinopathy include biomechanical reduction of stress on the tendon, relative rest, and ice since it is a vasoconstrictor (and increased vascularity is a finding in tendinopathy) and a natural analgesic. For example, the "RICE" regimen of Rest, Ice, Compression and Elevation is commonly used. Typical conventional treatments also include immobilization of the tendon, such as by the use of a splint or other internal or external structural support, to allow the tendon to heal. In some cases, the only treatment is a long period of rest (e.g., several months) to see if the condition will self-resolve.

Prior art treatments have focused on preserving healthy tendon, rather than treating degenerate tendons (e.g., one or more injections at the musculotendinous junction, where the tendon is not degenerate, to provide structure and support which limits movement and thus protects the healthy tendon). Placing limitations on movement are inconvenient for the patient but, more importantly, these treatments do not resolve the tendon degeneration but merely seek to stop the damage becoming worse. Conventional treatment protocols also suffer from significant disadvantages. For example, the use of corticosteroids can put the patient at risk for tendon rupture and the use of bracing, either internal or external, can have significant lifestyle implications. It would be beneficial if improved methods for treating tendinopathy could be provided.

BRIEF SUMMARY OF THE INVENTION

Methods and injectable compositions for treating tendon degeneration are described.

In one aspect, an injectable composition comprising a carbohydrate for treating an injured tendon in an animal or human is disclosed, wherein said composition comprises an effective amount of carbohydrate to increase tendon hydration and lubrication at the osteotendinous junction, when said composition is administered via intra-osteotendinous, or peri-osteotendinous injection.

In some embodiments, the composition is administered via peri-osteotendinous injection. In further embodiments, the composition is administered via intra-osteotendinous injection.

In some embodiments, the carbohydrate contains at least one functional group selected from the group consisting of thiols, alcohols, amines, carboxyl groups, aldehydes, amides, ester, ketones and combinations thereof.

In some embodiments, the carbohydrate has a molecular mass of about 10,000 to about 10,000,000 Daltons. In further embodiments, the carbohydrate has a molecular mass of about 300,000 to about 3,000,000 Daltons. In still further embodiments, the carbohydrate has a molecular mass of about 1,000,000 to about 3,000,000 Daltons.

In some embodiments, the carbohydrate is not cross-linked. In further embodiments, the carbohydrate comprises at least one cross-link. In further embodiments, the carbohydrate is at least about 1% by mole percent cross-linked. In further embodiments, the carbohydrate is between about 1% and about 10% by mole cross-linked. In further embodiments, the carbohydrate is between about 1% and about 5% by mole cross-linked. In further embodiments, the carbohydrate is about 1% by mole cross-linked. In further embodiments, the carbohydrate is about 2% by mole cross-linked. In further embodiments, the carbohydrate is about 3% by mole cross-linked. In further embodiments, the carbohydrate is about 4% by mole cross-linked. In further embodiments, the carbohydrate is about 5% by mole cross-linked.

In some embodiments, at least one cross-linker comprises a cross-linker selected from the group consisting of a carbodiimide cross-linker, a biscarbodiimide ("BCDI") cross-linker, a divinyl sulfone cross-linker, a diepoxy cross-linker, a disulfide cross-linker, a diglycidyl cross-linker, a diacrylate cross-linker, dialdehyde cross-linker, dianhydride cross-linker, diacylhalogen cross-linker, dimethacrylic acid anhydride cross-linker, diacrylic acid anhydride cross-linker and combinations thereof. In some embodiments, the at least one cross-linker comprises a cross-linker selected from the group consisting of a butanediol diepoxy ("BDDE") cross-linker, and a butanediol diglycidyl ether ("BDGE") cross-linker.

In some embodiments, the carbohydrate is autocross-linked.

In some embodiments, the carbohydrate is present in said composition at a concentration of about 1-100 mg/mL. In further embodiments, the carbohydrate is present in said composition at a concentration of about 2-30 mg/mL. In further embodiments, the carbohydrate is present in said composition at a concentration of about 5-30 mg/mL. In further embodiments, the carbohydrate is present in said composition at a concentration of about 10-20 mg/ml. In further embodiments, the carbohydrate is present in said composition at a concentration of about 12.5-17.5 mg/mL.

In some embodiments, the composition further comprises a pharmaceutically acceptable carrier. In further embodiments, the pharmaceutically acceptable carrier is selected from the group consisting of isotonic solutions or cryoperservative agents.

In some embodiments, the composition further comprises an additional agent. In some embodiments, the additional agent comprises a recombinant protein. In further embodiments, the additional agent comprises a small molecule. In further embodiments, the additional agent is selected from the group consisting of sorbitol, mannitol, an antioxidant (e.g., epigallocatechin gallate, resveratrol, curcumin), IGF-1, PDGF, VEGF, alpha-2-macroglobulin, and combinations thereof. In further embodiments, the additional agent comprises a stem cell. In further embodiments, the additional agent comprises a somatic cell. In further embodiments, the additional agent comprises a platelet rich plasma (PRP), platelet poor plasma (PPP), stem cell allografts, stem cell autografts, bone marrow aspirate (BMA), bone marrow aspirate concentrate (BMAC), autologous fibroblast or autologous myoblasts.

In some embodiments, the carbohydrate comprises at least one carbohydrate selected from the group consisting of collagen, gelatin, a polysaccharide, and combinations thereof.

In some embodiments, the carbohydrate comprises collagen. In some embodiments, the collagen comprises native collagen. In further embodiments, the collagen comprises denatured collagen.

In some embodiments, the carbohydrate comprises gelatin. In further embodiments, the gelatin comprises Type A gelatin. In still further embodiments, the gelatin comprises Type B gelatin. In some embodiments, the gelatin has a molecular mass of between about 80,000 Da and about 200,000 Da. In further embodiments, the gelatin has a polydispersity between about 1 and about 3. In still further embodiments, the gelatin has a polydispersity between about 1.1 and about 2.4.

In some embodiments, the carbohydrate comprises a polysaccharide. In further embodiments, the polysaccharide is selected from the group consisting of glycosaminoglycans and glucosaminoglycans. In still further embodiments, the polysaccharide is selected from the group consisting of dextran, heparan, heparin, hyaluronic acid, alginate, agarose, carrageenan, amylopectin, amylose, glycogen, starch, cellulose, chondroitin, dermatan, keratin, chitin, chitosan, carboxymethyl cellulose ("CMC"), xanthan gum, gellan gum, galactomannan, and combinations thereof. In some embodiments, the polysaccharide is a sulfated polysaccharide. In further embodiments, the sulfated polysaccharide is selected from the group consisting of sulfated HA, heparan sulfate, chondroitin sulfate, dextran sulfate, dermatan sulfate, keratan sulfate, and combinations thereof.

In some embodiments, the polysaccharide comprises more than about 10 monosaccharide residues joined to each other by glycosidic linkages.

In some embodiments, the polysaccharide has a molecular mass of between about 2,000 Da to about 8,000,000 Da. In further embodiments, the polysaccharide has a molecular mass of between about 20,000 Da and about 5,000,000 Da. In still further embodiments, the polysaccharide has a molecular mass of between about 1,000,000 Da and about 3,000,000 Da.

In some embodiments, the polysaccharide comprises a cross-linked carboxy polysaccharide.

In some embodiments, the polysaccharide comprises a percarboxylated polysaccharide.

In some embodiments, the carbohydrate comprises a polysaccharide. In some embodiments, the polysaccharide comprises dextran. In some embodiments, the dextran has a molecular mass of between about 300,000 Da to about 600,000 Da. In some embodiments, the dextran has a polydispersity between about 1 and about 3. In further embodiments, the dextran has a polydispersity between about 1.1 and about 2.4.

In some embodiments, the polysaccharide comprises hyaluronic acid, or an ester, acylurea, acyl isourea, disulfide, carbomer, or amide thereof. In some embodiments, the hyaluronic acid is selected from the group consisting of hyaluronan, sodium hyaluronate, potassium hyaluronate, magnesium hyaluronate, calcium hyaluronate, ammonium hyaluronate, and combinations thereof. In some embodiments, the hyaluronic acid comprises at least one cross-link. In some embodiments, the hyaluronic acid is derived from bacteria or animals (e.g., avian hyaluronic acid).

In some embodiments, the hyaluronic acid comprises a sulfated hyaluronic acid, or ester or amide thereof. In further embodiments, the hyaluronic acid comprises an N-sulfated hyaluronic acid, or ester or amide thereof.

In some embodiments, the hyaluronic acid comprises a hyaluronic ester. A hyaluronic ester is a hyaluronic acid molecule in which at least one carboxylate group of the hyaluronic acid is esterified with an alcohol. In some embodiments, the hyaluronic ester is an ester of hyaluronic acid with at least one alcohol selected from the group consisting of aliphatic, aryl-aliphatic, cycloaliphatic, aromatic, cyclic, and heterocyclic alcohols. In some embodiments, the hyaluronic ester has an esterification percentage from about 20 to about 100%, more particularly from about 50 to about 100% and in some cases from about 75 to about 100%. In some embodiments, the remaining non-esterified HA is salified with an organic or an inorganic base. See, e.g., European Patent No. 0 216 453 and U.S. Pat. No. 4,851,521, the contents of which are hereby incorporated by reference in their entireties. In some embodiments, the hyaluronic ester is represented by the formula (IX):

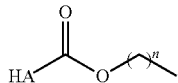

(IX)

wherein HA represents hyaluronic acid and n is an integer between 0 and 20. In some embodiments, the hyaluronic ester is selected from the group consisting of In some embodiments, the hyaluronic acid comprises a hyaluronic amide. A hyaluronic amide is a hyaluronic acid molecule in which at least one carboxylate group of the hyaluronic acid is amidated with an amine. In some embodiments, the hyaluronic amide is an amide of hyaluronic acid with at least one amide selected from the group consisting of aliphatic, aryl-aliphatic, cycloaliphatic, aromatic, cyclic, and heterocyclic amines. In some embodiments, the hyaluronic amide has an amidation percentage from about 0.1 to about 50%. In some embodiments, the remaining non-amidated HA is salified with an organic or an inorganic base. See European Patent No. 1 095 064, the contents of which are hereby incorporated by reference in their entirety. In some embodiments, the hyaluronic amide is represented by the formula (X):

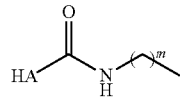

(X)

Hyaff7

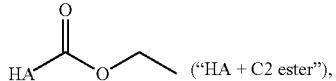 ("HA + C2 ester"),

Hyaff11

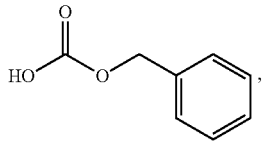,

Hyaff73

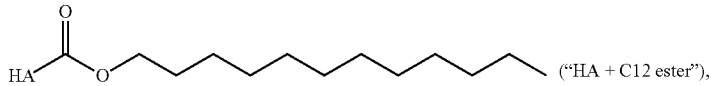 ("HA + C12 ester"),

Hyaff91

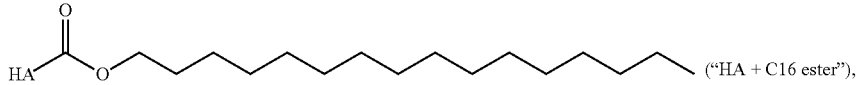 ("HA + C16 ester"),

Hyaff92

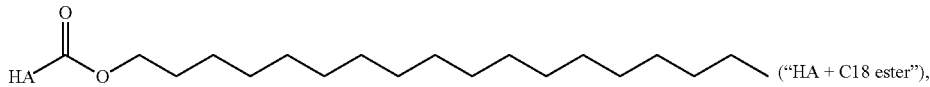 ("HA + C18 ester"),

Hyaff107

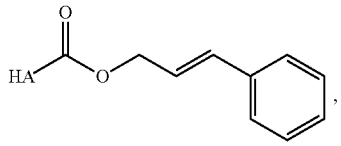,

Hyaff120

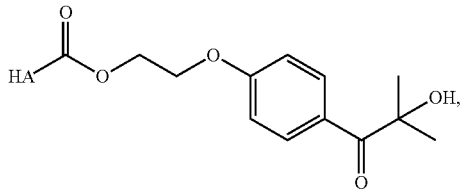

Hyaff302 (Hyaff11/P75+25% C16 ester), Hyaff303 (Hyaff11/P75+25% C18 ester), and Hyaff304 (Hyaff11/P75+25% C20 ester). The term "P75" as used herein indicates that 75 percent of the HA carboxylate groups are esterified.

wherein HA represents hyaluronic acid and m is an integer between 0 and 20. In some embodiments, the hyaluronic amide is selected from the group consisting of Hyadd1 ("HA+benzylamino amide"),

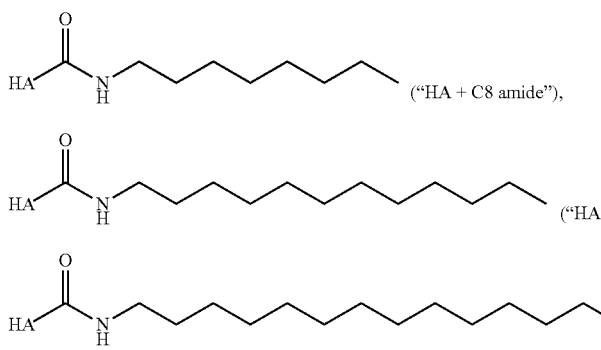

("HA + C8 amide"), ("HA + C12 amide"), and ("HA + C16 amide").

Hyadd2

Hyadd3

Hyadd4

In some embodiments, the carbohydrate is water-soluble. In some embodiments, the carbohydrate self-assembles in a micelle or a reverse-micelle.

In some embodiments, the composition is in the form of a hydrogel.

In some embodiments, the tendon is chronically injured and exhibits degenerative changes histologically. In some embodiments, histological changes manifest as deterioration of the condition of said tendon as measured by one or more of a visual analog scale ("VAS"), a disabilities of the arm, shoulder, and hand ("DASH") questionnaire, and patient-related tennis elbow evaluation ("PRTEE") questionnaire.

In some embodiments, the osteotendinous junction exhibits at least one degenerative characteristic selected from the group consisting of (i) an increase in Collagen III relative to normal tendon, (ii) a decrease in Collagen I relative to normal tendon, (iii) an increased observation of micro-tearing relative to normal tendon, (iv) an increase in disorganization of collagen micro-network relative to normal tendon, (v) an increase in fibroblastic infiltration relative to normal tendon (i.e., the degenerate portion of the tendon contains more fibroblasts per area than the non-degenerate portion), (vi) an increase in cell rounding relative to normal tendon, (vii) an increase in angiogenesis relative to normal tendon, (viii) an increase in cellularity relative to normal tendon, (ix) an increase in tendon gliding resistance relative to normal tendon, and (x) a dull gray appearance relative to normal tendon.

In some embodiments, administration of the composition physically reduces biomechanical interference. In further embodiments, administration of the composition biochemically reduces biomechanical interference.

In some embodiments, administration of the composition results in improvement of the condition of said tendon as measured by one or more of a visual analog scale ("VAS"), a disabilities of the arm, shoulder, and hand ("DASH") questionnaire, and patient-related tennis elbow evaluation ("PRTEE") questionnaire.

In some embodiments, the composition is used for treating tennis elbow. In further embodiments, the composition is used for treating rotator cuff tendinopathy, Achilles tendinopathy, patellar tendinopathy, as well as tendinopathies of the other tendons referenced in Table 1.

In some embodiments, the composition is for injection at a site distal from the musculotendinous junction.

In some embodiments, the composition is not administered via peri-musculotendinous or intra-musculotendinous injection.

In some embodiments, the composition is packaged in a syringe.

In another aspect, use of an injectable composition comprising a carbohydrate for treating an injured tendon in an animal or human is disclosed, wherein said composition comprises an effective amount of carbohydrate to increase tendon hydration and lubrication at the osteotendinous junction, when said composition is administered via intra-osteotendinous, or peri-osteotendinous injection.

In some embodiments, the composition is administered via peri-osteotendinous injection. In further embodiments, the composition is administered via intra-osteotendinous injection.

In some embodiments, the carbohydrate contains at least one functional group selected from the group consisting of thiols, alcohols, amines, carboxyl groups, aldehydes, ketones, esters, amides, and combinations thereof.

In some embodiments, the carbohydrate has a molecular mass of about 10,000 to about 10,000,000 Daltons. In further embodiments, the carbohydrate has a molecular mass of about 300,000 to about 3,000,000 Daltons. In still further embodiments, the carbohydrate has a molecular mass of about 1,000,000 to about 3,000,000 Daltons.

In another aspect, a syringe comprising a composition as disclosed herein is disclosed.

In another aspect, a kit comprising an injectable composition as disclosed herein or a syringe comprising a composition as disclosed herein and instructions for using said composition is disclosed herein.

In another aspect, disclosed herein is the administration of an injectable composition disclosed herein to a subject in need thereof.

In another aspect, a method for treating an injured tendon in a subject is disclosed herein, the method comprising: administering to a subject in need thereof an injectable composition comprising an effective amount of a carbohydrate as disclosed herein via intra-osteotendinous, or peri-osteotendinous injection.

In some embodiments, the method increases osteotendinous hydration and lubrication.

In some embodiments, the method increases range of motion in the subject. In some embodiments, range of motion is assessed by one or more of a visual analog scale ("VAS"), a disabilities of the arm, shoulder, and hand ("DASH") questionnaire, and patient-related tennis elbow evaluation ("PRTEE") questionnaire.

In some embodiments, the method does not restrict motion of the subject.

In some embodiments, pain on motion is decreased in said subject.

In some embodiments, patient satisfaction with patient outcome is increased. In some embodiments, physician satisfaction with patient outcome is increased.

In some embodiments, the injection comprises a single injection.

In some embodiments, the method comprises a plurality of injections of said composition at different times.

In some embodiments, the method comprises a first injection of said composition and a second injection of said composition, wherein the second injection is administered five to ten days after the first injection. In further embodiments, the second injection is administered one week after the first injection.

In some embodiments, the injection comprises a fanning injection. In further embodiments, the injection comprises a peppering injection. In accordance with some embodiments, the needle used for the injection will have a gauge from about 22-27, more particularly from about 25-27.

In some embodiments, the method further comprises post-injection joint manipulation immediately following injection. In some embodiments, the method further comprises post-injection joint manipulation one week to six months post-injection, more particularly one week to five months post-injection and in some cases from one week to four months post-injection. In further embodiments, the post-injection joint manipulation includes at least one of lateral rotation, medial rotation, flexion and extension. In some embodiments, the injection site is massaged immediately post-injection or regularly during recovery and rehabilitation.

BRIEF DESCRIPTION OF THE DRAWINGS

The following figures are provided for the purpose of illustration only and are not intended to be limiting.

DETAILED DESCRIPTION OF THE INVENTION

Figure 1:
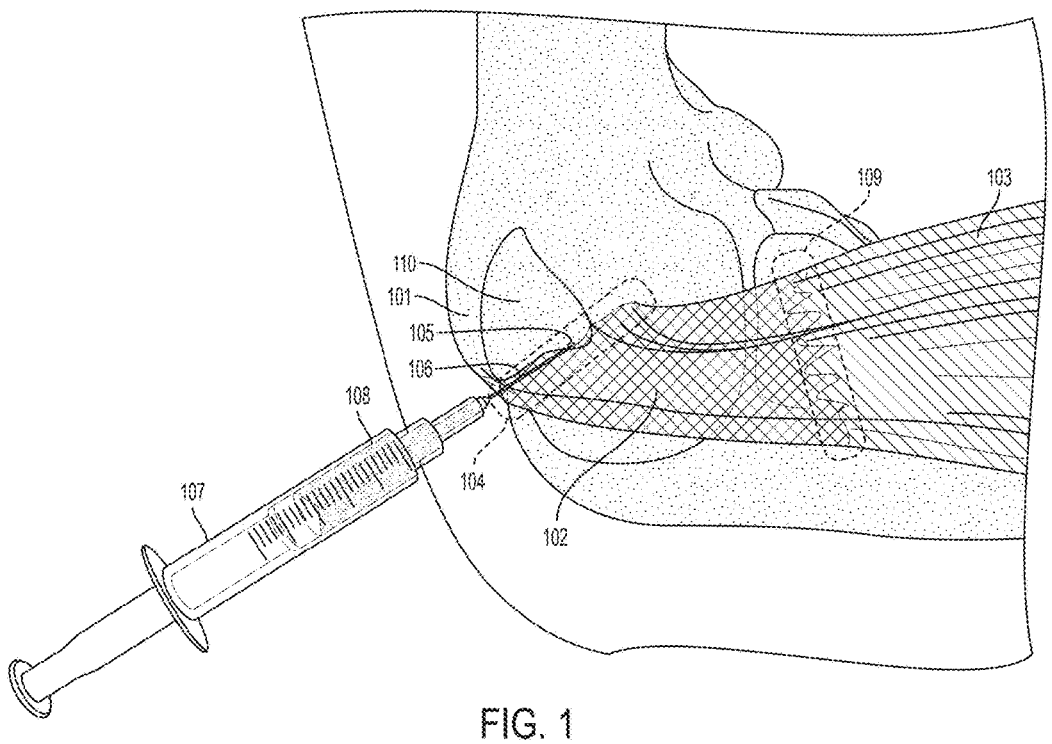
FIG. 1 shows a schematic of an exemplary embodiment of a peri-osteotendinous or intra-osteotendinous injection of a composition as disclosed herein for the treatment of an elbow tendinopathy.

The present disclosure relates to methods and injectable compositions for treating tendon degeneration. More particularly, the present disclosure relates to methods and injectable compositions for treating tendon degeneration in a human or animal via intra-osteotendinous or peri-osteotendinous injection. The disclosed injectable compositions include a carbohydrate that increases tendon hydration and lubrication at the tendon-bone interface. Furthermore, the presence of the carbohydrate creates an osmotic potential differential in the area resulting in an environment to which water will be drawn.

The present disclosure relates to methods of treating overuse injuries that result in the degeneration of the tendon at the osteotendinous junction. The "osteotendinous junction" refers to the anatomical location where the tendon attaches to the bone and where mechanical stress is concentrated. As a result of the overuse, the degeneration can be characterized, for example, by overuse-induced micro-tearing and/or the formation of collagen III fibrils within the well-organized and aligned collagen I fibers of the tendon at the tendon-bone interface. The formation of the collagen III fibrils introduces disorganization and interferes with normal biomechanics (e.g., gliding resistance, excursion resistance) at the location of the highest stress concentration (i.e., the osteotendinous junction) altering the normal stress distribution and biomechanics at this site. As a result of the unnatural stress state, further movement results in the stress being increasingly concentrated, resulting in greater micro-tearing and/or degeneration. Thus, with each movement, the mechanical properties of the tendon at the osteotendinous junction continue to deteriorate and degeneration increases, eventually reaching a point sufficient to cause the pain and loss of function associated with tendinopathy. Prior art treatments of tendinopathy have focused on immobilizing the tendon at the musculotendinous junction, including by the use of structural supports, splints and other means that do not address the impaired biomechanics at the osteotendinous junction. In fact, these treatments, by virtue of their being administered at the musculotendinous junction where the tendon is not degenerate (degeneration occurs at the osteotendinous junction), seek to stabilize healthy tendon at the musculotendinous junction, restricting movement and preventing healthy tendon degeneration. Importantly, and suboptimally, these treatments do not repair the degenerate tendon at the osteotendinous junction. Additionally, limiting movement of a patient can be inconvenient.

The inventors have surprisingly discovered that superior outcomes are attained by providing hydration and lubricity specifically to the tendon-bone interface in order to reduce biomechanical interference (e.g., tendon fibril gliding resistance, excursion resistance). In particular, by saturating the osteotendinous junction with a fluid retaining medium with high osmotic potential (e.g., a hydrogel), biomechanical interference (e.g., gliding resistance, excursion resistance) is reduced and a more normal stress distribution is created, allowing the degenerated tendon at the osteotendinous junction to recover without the need for immobilization of the tendon, resulting in relief of pain and restoration of function. In accordance with certain aspects, the present disclosure relates to methods for lubricating and hydrating degenerate tissue (e.g., tendon) at the region of maximal strain/biomechanical stress (e.g., the osteotendinous junction) to alleviate collagen disorganization. Unlike prior art treatments that have focused on the musculotendinous junction where the tendon is not degenerate, the present methods and compositions disclosed herein are directed to treating the osteotendinous junction, the site of maximum biomechanical strain and consequent tendon degeneration. The tendinopathy treatment disclosed herein facilitates movement of the degenerate tendon instead of further restricting movement of the healthy tendon, thereby providing improved results over prior art treatments. In particular, the injectable compositions and methods disclosed herein provide for increased motion, reduced pain, and better patient convenience, compliance, and outcomes as the patient should not undergo internal or external immobilization. Without wishing to be bound by theory, the inventors posit that the carbohydrates used in the injectable compositions and methods disclosed herein function to exert a lubricating effect by creating an environment of high osmotic potential at the insertion point, protecting the tendon from shear, torsional, tensional and compressive forces, augmenting the effect of carbohydrates and other components naturally present in the soft tissue surrounding damaged tendons and providing lubrication and hydration to the affected site, thereby providing a favorable environment for healing of the damaged tissue. In addition, the inventors posit that more normal stress distribution is created by reducing friction caused by the presence of the collagen III fibrils and/or collagen I production, which is accomplished by increasing fascicle separation specifically at the region of injection, which alleviates degeneration, pain, and restores function allowing the degenerate tendon to recover. The inventors have discovered that the injectable compositions and methods disclosed herein can also facilitate the natural movement that restores collagen I alignment by infiltrating the microtears to promote the formation of type I collagen instead of the weaker type III collagen present in degenerate tissue. The injectable compositions and methods disclosed herein alleviate the need for bracing or immobilization, whether internally or externally, and, unlike corticosteroids, pose no risk of tendon rupture. Moreover, the injectable compositions and methods disclosed herein can be administered in an office-based procedure with short latency and durable effect, providing a cost-effective alternative to surgery, e.g., for advanced-stage tendinopathy patients.

The terms "treatment," "treating," "treat," "therapy," "therapeutic," and the like are used herein to refer generally to attempting to obtain a desired pharmacological and/or physiological effect. The effect may be prophylactic in terms of completely or partially preventing or delaying the onset of a condition or symptom thereof and/or may be therapeutic in terms of a partial or complete stabilization, amelioration, or remedying of the condition or symptom.

The terms "osteotendinous junction," "OTJ," "tendon-bone interface," and "enthesis" are used interchangeably herein, and refer to the site of connection between tendon and bone. The OTJ provides a gradual transition from tendinous to bone tissue and can be virtually divided into four zones: (1) zone one, starting at the tendon side, includes aligned collagen I fibers and decorin, and exhibits tendon biomechanical properties; (2) zone two includes collagen types II and III, aggrecan and decorin, resembling fibrocartilage composition; (3) zone three includes mineralized fibrocartilage and is comprised of collagen types II and X and aggrecan; and (4) zone four includes mineralized collagen type I and is considered to be a bone protrusion, providing a dedicated connection point.

The term "carbohydrate" as used herein refers to polyhydroxy aldehydes and ketones comprised of carbon, hydrogen and oxygen. Carbohydrates include sugars, saccharides (such as monosaccharides, disaccharides, and polysaccharides), starches and cellulose. Exemplary carbohydrates include hyaluronic acid, chitosan, gelatin, dextran, alginate, carboxymethylcellulose, and cross-linked analogues of the same. In some embodiments the term "carbohydrate" as used herein encompasses polypeptides such as collagen, gelatin, and analogues of the same.

The term "biomechanical interference" as used herein refers to physical resistance with normal movement which can result in pain, discomfort, and/or reduced range of motion. In some embodiments, biomechanical interference is increased tendon fibril gliding resistance, and/or increased excursion resistance relative to normal tendon.

The term "pharmaceutically acceptable carrier," as used herein, refers to any and all solvents, dispersion media, coatings, antibacterial and antifungal agents, isotonic solutions, cryopreservative agents, and absorption delaying agents for pharmaceutical active substances as are well known in the art. The term "pharmaceutical" or "agent," as used herein, includes biological pharmaceuticals such as small molecules, proteins, peptides, and oligonucleotides. Except insofar as any conventional media or agent is incompatible with the agent, its use in the therapeutic pharmaceutical compositions is contemplated. Supplementary compounds or biological pharmaceuticals can also be incorporated into the pharmaceutical compositions.

The expression "therapeutically effective amount" refers to an amount of an agent disclosed herein, that is effective for preventing, ameliorating, remedying, treating or delaying the onset of a disease or condition.

The term "patient" as used herein refers to humans and non-humans such as primates, pets and farm animals.

The pharmaceutical compositions disclosed herein can be administered to any animal that can experience the beneficial effects of the compositions and methods disclosed herein. Such animals include humans and non-humans such as primates, pets and farm animals.

The term "intra-osteotendinous" as used herein refers to inside the tendon at the osteotendinous junction.

The term "peri-osteotendinous" as used herein refers to around the tendon at the osteotendinous junction.

The term "degenerative condition" as used herein refers to a tendon exhibiting at least one of the degenerate changes described herein. Degenerative conditions can also be identified based on histological changes, duration of symptoms and other clinical criteria (e.g., VAS, PRTEE, DASH scores) as known to one of ordinary skill in the art.

The term "tendon hydration" as used herein refers to increasing the water content of a tendon.

The term "tendon lubrication" as used herein refers to reducing the tendon biomechanical interference (e.g., tendon fibril gliding resistance, excursion resistance).

The term "autocross-linked" as used herein refers to the reaction of a carboxylate group of one HA molecule with an alcohol group of the same or a different HA molecule to form an ester.

The term "chronically injured tendon" as used herein refers to a tendon exhibiting at least one of the degenerate changes described herein. Degenerative conditions can also be identified based on histological changes, duration of symptoms and other clinical criteria (e.g., VAS, PRTEE, DASH scores) as known to one of ordinary skill in the art.

The term "degenerative changes" as used herein refers to characteristics such as the following (i) an increase in Collagen III relative to normal tendon, (ii) a decrease in Collagen I relative to normal tendon, (iii) an increased observation of micro-tearing relative to normal tendon, (iv) an increase in disorganization of collagen micro-network relative to normal tendon, (v) an increase in fibroblastic infiltration relative to normal tendon (i.e., the degenerate portion of the tendon contains more fibroblasts per area than the non-degenerate portion), (vi) an increase in cell rounding relative to normal tendon, (vii) an increase in angiogenesis relative to normal tendon, (viii) an increase in cellularity relative to normal tendon, (ix) an increase in tendon gliding resistance relative to normal tendon, and (x) a dull gray appearance relative to normal tendon. In some embodiments, degenerative changes can be determined based on clinical evaluations (e.g., VAS, PRTEE, DASH scores).

The term "restoration of function" as used herein refers to an improvement clinically as determined by any of the scores in the clinical examples (e.g., DASH, PRTEE, VAS, etc.).

The term "stem cell" as used herein refers to a cell that has the capacity to differentiate into at least bone, cartilage, and adipose tissue under appropriate conditions (e.g., in the presence of tissue-specific differentiation medium).

The term "somatic cell" refers to any other cell besides as stem cell.

Target Patient Profile

The methods and injectable compositions of the present disclosure are useful for treating tendon degeneration. Unlike certain prior art methods of treating tendons that were restricted to or only shown to be efficacious for patients with high levels of tendon use (e.g., tennis players and other athletes), the methods and compositions disclosed herein are useful for treating the whole spectrum of patients, regardless of how these patients use their tendons. In some embodiments, the tendon degeneration manifests as a tendinopathy. In some embodiments, the tendinopathy is of the lateral and/or medial epicondyle. In some embodiments, the tendon degeneration manifests as rotator cuff tendinopathy, Achilles tendinopathy, patellar tendinopathy, as well as tendinopathies of the other tendons referenced in Table 1. In some embodiments, the methods and injectable compositions described herein are particularly useful for treatment of a degenerative process that results in tendon degeneration at the osteotendinous junction. In some embodiments, the methods and injectable composition of the present disclosure provide for a repair process facilitated by natural biomechanics.

The methods and injectable compositions disclosed herein are useful in treating tendons exhibiting degenerative characteristics. In some embodiments, the degenerative characteristics of the tendons to be treated by the injectable compositions and methods disclosed herein are identified, qualified or quantified histologically. In some embodiments, histological changes manifest as: 1) increased pain compared to non-affected patients; 2) decreased function compared to non-affected patients; or 3) deterioration of the condition of said tendon as measured by one or more of a visual analog scale ("VAS"), a disabilities of the arm, shoulder, and hand ("DASH") questionnaire, and patient-related tennis elbow evaluation ("PRTEE") questionnaire. In some embodiments, the tendons to be treated by the methods and injectable compositions of the present disclosure exhibit one or more of the following degenerative characteristics at the osteotendinous junction: (i) an increase in Collagen III relative to normal tendon, (ii) a decrease in Collagen I relative to normal tendon, (iii) an increased observation of micro-tearing relative to normal tendon, (iv) an increase in disorganization of collagen micro-network relative to normal tendon, (v) an increase in fibroblastic infiltration relative to normal tendon, (vi) an increase in cell rounding relative to normal tendon, (vii) an increase in angiogenesis relative to normal tendon, (viii) an increase in cellularity relative to normal tendon, (ix) an increase in tendon gliding resistance relative to normal tendon, and (x) a dull gray appearance relative to normal tendon. In some embodiments, the degenerative characteristics of the tendons to be treated by the injectable compositions and methods disclosed herein are identified, qualified or quantified clinically, such as by use of a visual analog scale ("VAS," such as a 10 cm scale with 0 representing no pain and 10 representing maximal pain), by use of a disabilities of the arm, shoulder, and hand questionnaire ("DASH," such as a 5 point categorical scale with 1 representing no change in function and/or activity and 5 representing maximal change in normal function and/or activity), by patient-rated tennis elbow evaluation ("PRTEE") questionnaire (such as a 10 point categorical scale with 1 representing no pain and/or difficulty performing a task and 10 representing the worst imaginable pain or the inability to perform a task), by patients' global assessment of injury (such as a 5 point categorical scale with 1 representing no disability and 5 representing maximal disability), by patients' assessment of normal function and/or activity (such as a 5 point categorical scale with 1 representing no change in function and/or activity and 5 representing maximal change in normal function and/or activity), by physician's global assessment of injury (such as a 5 point categorical scale with 1 representing no impact of injury on function and 5 representing maximal impact of injury on function), by patient or physician satisfaction assessment (such as 10 point categorical scale with 1 representing no satisfaction with the procedure and 10 representing very high satisfaction with the procedure), by review of a patient diary and return to pain and disability-free sport, or combinations thereof.

In some embodiments, the injectable compositions disclosed herein are useful for the treatment of tendinopathy of one or more of the tendons listed in Table 1:

TABLE 1

| Functional Area | Tendon |
| --- | --- |
| Shoulder (Rotator Cuff) | Teres Minor Tendons |
| | Infraspinatus Tendons |
| | Supraspinatus Tendons |
| | Subscapularis Tendons |
| Elbow/Forearm | Deltoid Tendons |
| | Biceps Tendons |
| | Triceps Tendons |
| | Brachioradialis Tendons |
| | Extensor Carpi Radialis Brevis Tendons |
| | Extensor Carpi Radialis Longus Tendons |
| | Supinator Tendons |
| Wrist | Flexor Carpi Radialis Tendons |
| | Flexor Carpi Ulnaris Tendons |
| | Extensor Capri Radialis Tendons |
| | Extensor Carpi Radialis Brevis Tendons |
| Hip/Groin | Iliopsoas Tendons |
| | Obturator Internus Tendons |
| | Adductor Longus, Brevis, and Magnus Tendons |
| | Gluteus Maximus and Gluteus Medius Tendons |
| | Iliotibial Band |
| Knee | Quadriceps Tendons |
| | Patellar Tendons |
| | Hamstring Tendons |
| | Sartorius Tendons |
| Ankle | Gastrocnemius Tendons |
| | Achilles Tendons |
| | Soleus Tendons |
| | Tibialis Anterior Tendons |
| | Peroneus Longus Tendons |
| Hand (Fingers) | Flexor Digitorum Longus Tendons |
| | Interosseus Tendons |
| | Flexor Digitorum Profundus Tendons |
| | Abductor Digiti Minimi Tendons |
| Hand (Thumb) | Opponens Pollicis Tendons |
| | Flexor Pollicis Tendons |
| | Extensor and Abductor Pollicis Tendons |

TABLE 1-continued

| Functional Area | Tendon |
|---|---|
| Foot (Toes) | Flexor Hallucis Longus Tendons |
| | Flexor Digitorum Brevis Tendons |
| | Lumbrical Tendons |
| | Abductor Hallucis Tendons |
| | Flexor Digitorum Longus Tendons |
| | Abductor Digiti Minimi Tendons |
| | Plantar Fasciitis |
| Back | Multifidus Tendons |
| | Quadratus Lumborum Tendons |
| | Longissmus Thoracis Tendons |
| | Iliocostalis Tendons |
| | Spinalis Thoracis Tendons |
| | Psoas Major Tendons |

In some embodiments, the injectable composition is used to treat tendinopathy of the lateral or medial epicondyle of the elbow. In some embodiments, the injectable composition is used to treat tendinopathy of the rotator cuff tendon, Achilles tendon, or patellar tendon.

Routes of Administration

The present disclosure relates, in part, to the administration of the compositions disclosed herein via intra-osteotendinous or peri-osteotendinous injection.

To prepare for an injection for the treatment of tendinopathy in a patient, the tendon is palpated around the osteotendinous junction. This location is the site of highest stress concentration at the region where tendon attaches to bone. It is this stress concentration at the hard tissue interface which makes the tendon vulnerable to further degeneration and eventual rupture. This location can vary in area, depending on the location and the patient, but is the location where the tendon joins the bone.

Once the osteotendinous junction is identified, the injection site is identified. In some embodiments, the injection site is directly above the osteotendinous junction. In further embodiments, the injection site is less than about 0.50 cm from the proximal point directly above the osteotendinous junction. In still further embodiments, the injection site is less than about 1.00 cm from the proximal point directly above the osteotendinous junction. In still further embodiments, the injection site is less than about 0.10 cm, less than about 0.20 cm, less than about 0.30 cm, less than about 0.40 cm, less than about 0.50 cm, less than about 0.60 cm, less than about 0.70 cm, less than about 0.80 cm, less than about 0.90 cm, or less than about 1.00 cm from the proximal point directly above the osteotendinous junction. In some embodiments, the injection site is distal from the musculotendinous junction (i.e., where the tendon meets muscle). In some embodiments, the injection site is more than 1.00 cm from the lateral epicondyle. In some embodiments, the injection site is located using a two-dimensional framing technique.

Once the injection site is identified, the needle is inserted through the skin at the injection site and the composition is injected. In some embodiments, the needle is inserted into the peri-osteotendinous space above the osteotendinous junction and the composition is injected into the peri-osteotendinous space above the osteotendinous junction. In further embodiments, the needle is inserted intra-osteotendinously at the osteotendinous junction and the composition is injected into the tendon at the osteotendinous junction. In still further embodiments, the needles is inserted intra-osteotendinously proximal to the osteotendinous junction and the composition is injected into the tendon proximal to the osteotendinous junction. In some embodiments, the composition is injected into the tendon less than about 0.50 cm from the proximal point in the osteotendinous junction. In some embodiments, the composition is injected into the tendon less than about 1.00 cm from the proximal point in the osteotendinous junction. In some embodiments, the composition is injected into the tendon less than about 0.10 cm, less than about 0.20 cm, less than about 0.30 cm, less than about 0.40 cm, less than about 0.50 cm, less than about 0.60 cm, less than about 0.70 cm, less than about 0.80 cm, less than about 0.90 cm, or less than about 1.00 from the proximal point in the osteotendinous junction. In some embodiments, the composition is injected proximal to the lateral epicondyle. In some embodiments, the composition is injected into the tendon less than about 1.00 cm from the lateral epicondyle. In some embodiments, the composition is injected into the tendon less than about 0.10 cm, less than about 0.20 cm, less than about 0.30 cm, less than about 0.40 cm, less than about 0.50 cm, less than about 0.60 cm, less than about 0.70 cm, less than about 0.80 cm, less than about 0.90 cm, or less than about 1.00 from the lateral epicondyle.

Because the volume that the composition can occupy is limited, several injection techniques can be used to increase the volume injected and coverage. For example, for peri-osteotendinous injection, once the needle is inserted under the skin, the needle can be fanned (e.g., the needle is inserted and pulled back slightly while a portion of the composition is dispensed; the needle is then rotated 90-180 degrees ("fanned") and the remainder of the composition is injected.). Another technique is to "pepper" the osteotendinous junction with multiple injections in proximity to one another, either peri-osteotendinously or intra-osteotendinously, injecting a portion of the composition at each injection site. In some embodiments, the injection site is in the region of pain. In further embodiments, the region of most pain is peppered with multiple injections. In some embodiments, the injection site is distal to the region of pain. In further embodiments, the injection site is proximal to the region of pain. In some embodiments, the composition is administered in a single injection. In some embodiments, the injection is repeated after a period of one day to one month. In some embodiments, the injection is repeated after a period of one week. In some embodiments, the injection is repeated after a period of two weeks. In some embodiments, the injection is repeated after a period of three weeks. In some embodiments, injections are provided at a plurality of depths.

Various needle gauges can be used in connection with the present disclosure. The use of smaller gauge needles can be useful to minimize both tissue trauma during injection and patient discomfort. In some embodiments, a needle useful in connection with the present disclosure is smaller than 18 gauge. In further embodiments, a needle useful in connection with the present disclosure is smaller than 20 gauge. In still further embodiments, a needle useful in connection with the present disclosure is smaller than 22 gauge. In still further embodiments, a needle useful in connection with the present disclosure is smaller than 25 gauge. In still further embodiments, a needle useful in connection with the present disclosure is smaller than 27 gauge.

In some embodiments, the injectable composition is delivered in a single injection. In some embodiments, the injectable composition is delivered in two injections. In some embodiments, the injectable composition is delivered in three injections. In some embodiments, the injectable composition is delivered in four injections. In some embodiments, the injectable composition is delivered in five injections. In some embodiments, the injections are administered contemporaneously. In further embodiments, the injections are administered non-contemporaneously. In some embodiments, the non-contemporaneous administration encompasses a period of between about one day to about six months. In some embodiments, the non-contemporaneous administration encompasses a period of about one week. In some embodiments, the non-contemporaneous administration encompasses weekly injections. In some embodiments, the non-contemporaneous administration encompasses injections every other day.

Various volumes of composition can be injected in connection with the present disclosure. The volume injected without causing patient discomfort may be limited due to space limitations in the tissue to be treated. In some embodiments, less than about 10.0 mL of the composition is injected. In further embodiments, less than about 9.0 mL of the composition is injected. In further embodiments, less than about 8.0 mL of the composition is injected. In further embodiments, less than about 7.0 mL of the composition is injected. In further embodiments, less than about 6.0 mL of the composition is injected. In some embodiments, less than about 5.0 mL of the composition is injected. In further embodiments, less than about 4.0 mL of the composition is injected. In further embodiments, less than about 3.0 mL of the composition is injected. In further embodiments, less than about 2.0 mL of the composition is injected. In further embodiments, less than about 1.0 mL of the composition is injected. In further embodiments, less than about 0.8 mL of the composition is injected. In further embodiments, less than about 0.5 mL of the composition is injected. In further embodiments, less than about 0.4 mL of the composition is injected. In further embodiments, less than about 0.3 mL of the composition is injected. In further embodiments, less than about 0.2 mL of the composition is injected. In further embodiments, less than about 0.1 mL of the composition is injected.

In some embodiments, each injection includes about 1 mL of the injectable composition. In some embodiments, each injection includes about 2 mL of the injectable composition. In some embodiments, each injection includes about 3 mL of the injectable composition. In some embodiments, each injection includes about 4 mL of the injectable composition. In some embodiments, each injection includes about 5 mL of the injectable composition. In some embodiments, each injection includes about 6 mL of the injectable composition. In some embodiments, each injection includes about 7 mL of the injectable composition. In some embodiments, each injection includes about 8 mL of the injectable composition. In some embodiments, each injection includes about 9 mL of the injectable composition. In some embodiments, each injection includes about 10 mL of the injectable composition. In some embodiments, the total volume of injectable composition injected is about 1 mL. In some embodiments, the total volume of injectable composition injected is about 2 mL. In some embodiments, the total volume of injectable composition injected is about 3 mL. In some embodiments, the total volume of injectable composition injected is about 4 mL. In some embodiments, the total volume of injectable composition injected is about 5 mL. In some embodiments, the total volume of injectable composition injected is about 6 mL. In some embodiments, the total volume of injectable composition injected is about 7 mL. In some embodiments, the total volume of injectable composition injected is about 8 mL. In some embodiments, the total volume of injectable composition injected is about 9 mL. In some embodiments, the total volume of injectable composition injected is about 10 mL.

In some embodiments, an analgesic is applied at or around the injection site prior to the injection of the compositions disclosed herein. In some embodiments, the analgesic is lidocaine. In some embodiments, the patient is anesthetized. In some embodiments, the injection is performed under imaging guidance (e.g., fluroscopy, ultrasound).

Methods of Preparation

Methods of preparing various compositions with a certain amount of active ingredients are known, or will be apparent in light of this disclosure, to those skilled in the art. Methods of preparing said compositions can incorporate other suitable pharmaceutical excipients and their formulations as described in Remington's Pharmaceutical Sciences, Martin, E. W., ed., Mack Publishing Company, 19th ed. (1995).

One of ordinary skill in the art will appreciate that a method of administering effective amounts of the injectable compositions disclosed herein to a patient in need thereof, can be determined empirically, or by standards currently recognized in the medical arts. The compositions disclosed herein can be administered to a patient as compositions in combination with one or more pharmaceutically acceptable excipients. It will be understood that, when administered to a human patient, the total daily usage of the compositions disclosed herein will be decided within the scope of sound medical judgment by the attending physician. The specific therapeutically effective dose level for any particular patient will depend upon a variety of factors: the type and degree of the response to be achieved; activity of the specific composition employed; the specific composition employed; the age, body weight, general health, gender and diet of the patient; the time of administration, and rate of excretion of the composition or components thereof; the duration of the treatment; drugs used in combination or coincidental with the specific composition; and like factors well known in the medical arts. It is well within the skill of the art to start doses of the compositions disclosed herein at levels lower than those required to achieve the desired therapeutic effect and to gradually increase the dosages until the desired effect is achieved.

Dosing can also be determined in a patient-specific manner to provide a predetermined concentration of the composition in the treated area, as determined by techniques accepted and routine in the art.

Dosage Determinations

In general, the injectable compositions disclosed herein may be used alone or in concert with other therapeutic agents at appropriate dosages defined by routine testing in order to obtain optimal efficacy while minimizing any potential toxicity. The dosage regimen utilizing an injectable composition disclosed herein may be selected in accordance with a variety of factors including type, species, age, weight, sex, medical condition of the patient; the severity of the condition to be treated; the route of administration; and the particular injectable composition employed. A physician or veterinarian of ordinary skill can readily determine and prescribe the effective amount of the injectable composition required to prevent, counter, or arrest the progress of the condition.

Carbohydrates

The injectable compositions of the present disclosure include a carbohydrate. Various carbohydrates can be used in connection with the present disclosure. In some embodiments, injection of the carbohydrate provides lubrication and hydration. In some embodiments, the carbohydrate is hyaluronic acid, chitosan, gelatin, dextran, alginate, carboxymethylcellulose, and combinations thereof. In some embodiments, the carbohydrate disclosed herein has a molecular mass of about 10,000 to about 10,000,000 Daltons. In further embodiments, the carbohydrate disclosed herein has a molecular mass of about 300,000 to about 3,000,000 Daltons. In still further embodiments, the carbohydrate disclosed herein has a molecular mass of about 1,000,000 to about 3,000,000 Daltons. In some embodiments, the carbohydrate has a molecular mass of at least about 3,000,000 Daltons after sterilization.

In some embodiments, the injectable composition includes at least about 1 mg of a carbohydrate. In some embodiments, the injectable composition includes at least about 5 mg of a carbohydrate. In some embodiments, the injectable composition includes at least about 10 mg of a carbohydrate. In some embodiments, the injectable composition includes at least about 20 mg of a carbohydrate. In some embodiments, the injectable composition includes less than about 100 mg of a carbohydrate. In some embodiments, the injectable composition includes less than about 80 mg of a carbohydrate. In some embodiments, the injectable composition includes less than about 60 mg of a carbohydrate. In some embodiments, the injectable composition includes less than about 50 mg of a carbohydrate. In some embodiments, the injectable composition includes less than about 40 mg of a carbohydrate. In some embodiments, the injectable composition includes less than about 30 mg of a carbohydrate. In some embodiments, the injectable composition includes less than about 20 mg of a carbohydrate. In some embodiments, the injectable composition includes less than about 10 mg of a carbohydrate. In some embodiments, the injectable composition includes less than about 5 mg of a carbohydrate. In some embodiments, the injectable composition includes about 20 mg to about 80 mg of the carbohydrate. In some embodiments, the injectable composition includes about 24 mg of the carbohydrate. In some embodiments, the injectable composition includes about 30 mg of the carbohydrate. In some embodiments, the injectable composition includes about 40 mg of the carbohydrate. In some embodiments, the injectable composition includes about 60 mg of the carbohydrate. In some embodiments, the injectable composition includes about 80 mg of the carbohydrate.

In some embodiments, the injectable composition is provided as a single dose. In some embodiments, the injectable composition is provided in multiple doses.

In some embodiments, the injectable composition includes a carbohydrate at a concentration of about 1-100 mg/mL. In further embodiments, the injectable composition includes a carbohydrate at a concentration of about 1-50 mg/mL. In further embodiments, the injectable composition includes a carbohydrate at a concentration of about 2-30 mg/mL. In further embodiments, the injectable composition includes a carbohydrate at a concentration of about 5-30 mg/mL. In further embodiments, the injectable composition includes a carbohydrate at a concentration of about 12.5-17.5 mg/mL. In further embodiments, the injectable composition includes a carbohydrate at a concentration of about 1-20 mg/mL. In further embodiments, the injectable composition includes a carbohydrate at a concentration of about 1-10 mg/mL. In further embodiments, the injectable composition includes a carbohydrate at a concentration of about 1-5 mg/mL.

In some embodiments, the carbohydrate is present in the composition at a concentration of between about 0.01 µM and about 100 mM. In further embodiments, the carbohydrate is present in the composition at a concentration of between about 0.01 mM and about 50 mM. In further embodiments, the carbohydrate is present in the composition at a concentration of between about 0.1 mM and about 25 mM. In further embodiments, the carbohydrate is present in the composition at a concentration of between about 0.01 mM and about 10 mM. In further embodiments, the carbohydrate is present in the composition at a concentration of between about 1 mM and about 10 mM. In some embodiments, the carbohydrate is present in the composition at a concentration of between about 0.01 µM and about 1 mM. In further embodiments, the carbohydrate is present in the composition at a concentration of between about 0.1 µM and about 500 µM. In further embodiments, the carbohydrate is present in the composition at a concentration of between about 1 µM and about 250 µM. In further embodiments, the carbohydrate is present in the composition at a concentration of between about 1 µM and about 100 µM. In further embodiments, the carbohydrate is present in the composition at a concentration of between about 1 µM and about 50 µM.

In some embodiments, the carbohydrates and/or injectable compositions disclosed herein are sterilized and/or aseptically processed. Sterilization can be accomplished using conventional sterilization procedures known in the art. In some embodiments, the carbohydrate and/or injectable composition is sterilized by ethylene oxide sterilization, irradiation (such as gamma irradiation), hydrogen peroxide sterilization, heat sterilization, sterile filtration, and other such methods know in the art. In some embodiments, the heat sterilization is accomplished by autoclave. In further embodiments, the heat sterilization is accomplished by steam sterilization. In some embodiments, injection of compressed air is used during sterilization to artificially raise the pressure and prevent boil over. In further embodiments, a sterile carbohydrate and/or injectable composition can be obtained by using all sterile components and carrying out all reactions and manipulations in under aseptic conditions. In some embodiments, the carbohydrate and/or injectable composition is steam sterilized. In some embodiments, the carbohydrate and/or injectable composition is sterile filtered.

In accordance with certain embodiments, the carbohydrates may contain a functional group. Examples of useful functional groups include: thiols, alcohols, amines, aldehydes, amides, esters, ketones, and carboxyl groups.

In some embodiments, the carbohydrate is cross-linked. Cross-linking refers to the connection of linear carbohydrates to one another by a cross-linker. In some embodiments, cross-linking is accomplished by derivatizing the functional groups of the carbohydrate. In some embodiments, at least a portion of the functional groups of the carbohydrate are each independently derivatized. In some embodiments, at least a portion of the carboxyl groups of the carbohydrate are functionalized to include an N-acylurea or O-acyl isourea, or both N-acylurea and O-acyl isourea. N-acylurea and O-acyl isourea derivatives are shown in the bracketed fragments in the following structural formulas (I) and (II):

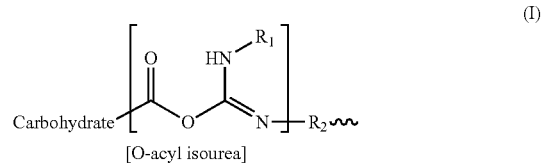

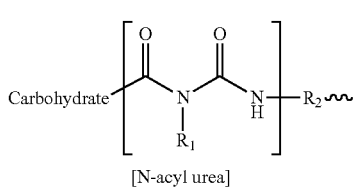

[N-acyl urea]

In structural formulas (I) and (II), each $R_1$ can be the same or different. Each $R_1$ is selected from the group consisting of hydrogen; substituted or unsubstituted hydrocarbyl groups (linear or branched, or cyclic or acyclic) optionally interrupted by one or more heteroatoms; substituted or unsubstituted alkoxy; substituted or unsubstituted aryloxy; and substituted or unsubstituted aralkyloxy. Examples of substituted or unsubstituted hydrocarbyl groups (linear or branched, or cyclic or acyclic) optionally interrupted by one or more heteroatoms include optionally substituted aliphatic groups (e.g., alkyl, alkenyl, alkynyl, cycloalkyl, cycloalkenyl, cycloalkynyl and cycloaliphaticalkyl); optionally substituted aryl groups (including heteroaryl groups); optionally substituted aliphatic groups interrupted by one or more heteroatoms (e.g., heterocyclyl, cycloaliphaticalkyl and heterocyclylalkyl); and optionally substituted, partially aromatic and partially aliphatic groups (e.g., aralkyl and heteroaralkyl). Suitable optional substituents do not substantially interfere with the properties of the resulting cross-linked carbohydrate composition. Suitable substituents for carbon atoms of hydrocarbyl groups include —OH, halogens (—Br, —Cl, —I, —F), —OR$^a$, —O—COR$^a$, —COR$^a$, —CN, —NCS, —NO$_2$, —COOH, —SO$_3$H, —NH$_2$, —NHR$^a$—N(R$^a$R$^b$), —COOR$^a$, —CHO, —CONH$_2$, —CONHR$^a$, —CON(R$^a$R$^b$), —NHCOR$^a$, —NR$^b$COR$^a$, —NHCONH$_2$, —NHCONR$^a$H, —NHCON(R$^a$R$^b$), —NR$^b$CONH$_2$, —NR$^b$CONR$^a$H, —NR$^c$CON(R$^a$R$^b$), —C(=NH)—NH$_2$, —C(=NH)—NHR$^a$, —C(=NH)—N(R$^a$R$^b$), —C(=NR$^c$)—NH$_2$, —C(=NR$^c$)—NHR$^a$)—C(—NR$^c$)—N(R$^a$R$^b$), —NH—C(=NH)—NH$_2$, —NH—C(=NH)—NH$_2$, —NH—C(=NH)—NHR$^a$, —NH—C(=NH)—N(R$^a$R$^b$), —NH—C(=NR$^c$)—NH$_2$, —NH—C(=NR$^c$)—NHR$^a$, —NH—C(=NR$^c$)—N(R$^a$R$^b$), —NR$^d$H—C(=NH)—NH$_2$, —NR$^d$—C(=NH)—N(R$^a$R$^b$), —NR$^d$—C(=NR$^c$)—NH$_2$, —NR$^d$—C(=NR$^c$)—NHR$^a$, —NR$^d$—C(=NR$^c$)—N(R$^a$R$^b$), —NHNH$_2$, —NHNHR$^a$, —NHR$^a$R$^b$, —SO$_2$NH$_2$, —SO$_2$NHR$^a$, —SO$_2$NR$^a$R$^b$, —SH, —SR$^a$, —S(O)R$^a$, and —S(O)$_2$R$^a$. In addition, an alkyl, alkylene, alkenyl or alkenylene group can be substituted with substituted or unsubstituted aryl group to form, for example, an aralkyl group such as benzyl. Similarly, aryl groups can be substituted with a substituted or unsubstituted alkyl or alkenyl group.

R$^a$-R$^d$ are each independently an alkyl group, aryl group, including heteroaryl group, non-aromatic heterocyclic group or —N(R$^a$R$^b$), taken together, form a substituted or unsubstituted non-aromatic heterocyclic group. The alkyl, aromatic and non-aromatic heterocyclic group represented by R$^a$—R$^d$ and the non-aromatic heterocyclic group represented by —N(R$^a$R$^b$) can optionally be substituted.

In other embodiments, $R_1$ is an optionally substituted aliphatic group (cyclic or acyclic, or linear or branched). In some embodiments, $R_1$ is an alkyl group, such as $C_1$-$C_6$ alkyl (e.g., methyl, ethyl, propyl, butyl, 2-propyl, tert-butyl, and the like). In some embodiments, each $R_1$ is ethyl.

Each $R_2$ is independently a substituted or unsubstituted linking group including one or more of hydrocarbylene groups (cyclic or acyclic, or linear or branched) optionally interrupted by one or more heteroatoms. Examples include optionally substituted aliphatic groups (e.g., alkylene, alkenylene, alkynylene, cycloalkylene, cycloalkenylene, cycloalkynylene and cycloaliphaticalkylene); optionally substituted arylene (including heteroaryl groups); optionally substituted aliphatic groups interrupted by one or more heteroatoms (e.g., heterocyclylene, cycloaliphaticalkylene and heterocyclylalkylene); and optionally substituted, partially aromatic and partially aliphatic groups (e.g., aralkylene and heteroaralkylene). Certain suitable optional substituents are described above for $R_1$.

In some embodiments, $R_2$ includes or is interrupted by other groups, e.g., carbonyl, amide, oxy, sulfide, disulfide, and the like. In other embodiments, $R_2$ is a cycloaliphatic, arylene, heteroarylene, or heterocyclylene group. In still other embodiments, $R_2$ is 1,6-hexamethylene, octamethylene, decamethylene, dodecamethylene, PEG, —CH$_2$CH$_2$—S—S—CH$_2$CH$_2$—, para-phenylene-S—S-para-phenylene, meta-phenylene-S—S-meta-phenylene, ortho-phenylene-S—S-ortho-phenylene, ortho-phenylene, meta-phenylene or para-phenylene. In some embodiments, $R_2$ is phenylene. In further embodiments, $R_2$ is para-phenylene.

In one embodiment, the wavy line connected to $R_2$ in structural formulas (I) and (II) represents hydrogen, substituted or unsubstituted hydrocarbyl groups (linear or branched, or cyclic or acyclic) optionally interrupted by one or more heteroatoms; alkoxy; aryloxy; or aralkyloxy, as described for $R_1$. In another embodiment, the wavy line connected to $R_2$ in structural formulas (I) and (II) represents optionally substituted N-acyl urea group or O-acyl isourea group, as shown below in structural formulas VI-VIII.

In some embodiments, the modified carbohydrate derivative is prepared by reacting the carbohydrate with a carbodiimide. In some embodiments, the carbodiimide is a multifunctional carbodiimide. In further embodiments, the carbodiimide is a biscarbodiimide ("BCDI").

Examples of suitable carbodiimide include a monocarbodiimide and a multifunctional carbodiimide, such as a biscarbodiimide. The monocarbodiimide has the formula:

wherein $R_3$ and $R_4$ are each independently as described above for $R_1$ (e.g., hydrocarbyl, substituted-hydrocarbyl, alkoxy, aryloxy or alkaryloxy). Examples of suitable monocarbodiimides include: 1-ethyl-3-(3-dimethylaminopropyl)-carbodiimide hydrochloride (EDC); 1-cyclohexyl-3-(2-morpholinoethyl)carbodiimide metho-p-toluenesulfonate (CMC); 1-(3-(dimethylamino)propyl)-3-ethylcarbodiimide methiodide (EAC); 1,3-dicyclohexylcarbodiimide (DCC); and 1-benzyl-3-(3-dimethylaminopropyl) carbodiimide hydrochloride (BDC).

Examples of suitable biscarbodiimides may be represented by those difunctional compounds having the formula:

Each $R_1$ can be different or the same. $R_1$ and $R_2$ are each independently as described above. Suitable specific examples of biscarbodiimides include 1,6-hexamethylene bis(ethylcarbodiimide), 1,8-octamethylene bis(ethylcarbodiimide), 1,10 decamethylene bis(ethylcarbodiimide), 1,12 dodecamethylene bis(ethylcarbodiimide), PEG-bis(propyl (ethylcarbodiimide)), 2,2'-dithio-bis(ethyl(ethylcarbodiimde)), 1,1'-dithio-ortho-phenylene-bis(ethylcarbodiimide), 1,1'-dithio-para-phenylene-bis(ethylcarbodiimide), and 1,1'-dithio-meta-phenylene bis(ethylcarbodiimide). In some embodiments, the biscarbodiimide is para-phenylene-bis (ethylcarbodiimide). Methods of preparing biscarbodiimides are described, for example, in U.S. Pat. Nos. 6,013,679; 2,946,819; 3,231,610; 3,502,722; 3,644,456; 3,972,933; 4,014,935; 4,066,629; 4,085,140; 4,096,334; 4,137,386, 6,548,081, and 6,620,927 the contents of which are incorporated herein by reference in their entireties.

In some embodiments, the cross-linker comprises divinyl sulfone. In further embodiments, the cross-linker comprises a diepoxy cross-linker. In some embodiments, the cross-linker comprises a butanediol diepoxy ("BDDE") cross-linker. In some embodiments, the cross-linker comprises a butanediol diglycidyl ether ("BDGE") cross-linker. In some embodiments, the cross-linker comprises a 1,4-butanediol diglycidyl ether. In some embodiments, the cross-linker is selected from the group consisting of a dialdehyde cross-linker, a dianhydride cross-linker, a diacylhalogen cross-linker, a dimethacrylic acid anhydride cross-linker, and a diacrylic acid anhydride cross-linker.

In some embodiments, the carbohydrate is autocross-linked. In some embodiments, the carbohydrate is autocross-linked via the use of a carbodiimide.

In one embodiment, the carbohydrate derivative is cross-linked. In another embodiment, the carbohydrate derivative is at least about 1% by mole cross-linked, and the carbohydrate derivative includes at least one cross-link, e.g., the linking group connecting through a group U at each end to a Carbohydrate molecule, as shown in the following structural formula (V):

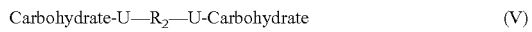

Carbohydrate-U—$R_2$—U-Carbohydrate     (V)

In further embodiments, the carbohydrate derivative is between 0% and 20% by mole cross-linked. In further embodiments, the carbohydrate derivative is between 0% and 10% by mole cross-linked. In further embodiments, the carbohydrate derivative is between 1% and 10% by mole cross-linked. In further embodiments, the carbohydrate derivative is between 1% and 5% by mole cross-linked. In further embodiments, the carbohydrate derivative is between 1% and 2.5% by mole cross-linked. In further embodiments, the carbohydrate derivative is 1% by mole cross-linked. In further embodiments, the carbohydrate derivative is 2% by mole cross-linked. In further embodiments, the carbohydrate derivative is 3% by mole cross-linked. In further embodiments, the carbohydrate derivative is 4% by mole cross-linked. In further embodiments, the carbohydrate derivative is 5% by mole cross-linked. In further embodiments, the carbohydrate derivative is 6% by mole cross-linked. In further embodiments, the carbohydrate derivative is 7% by mole cross-linked. In further embodiments, the carbohydrate derivative is 8% by mole cross-linked. In further embodiments, the carbohydrate derivative is 9% by mole cross-linked. In further embodiments, the carbohydrate derivative is 10% by mole cross-linked.

In another embodiment, at least about 1% by mole, such as at least about 2% by mole, at least about 5% by mole, or between about 1% by mole and about 20% by mole, of the functional groups of the modified carbohydrate acid are derivatized. In yet another embodiment, at least about 25% by mole, such as between about 25% by mole and about 75% by mole, of the derivatized functionalities are O-acylisoureas and/or N-acylureas. In yet another embodiment, the functional groups of the modified carbohydrate are derivatized, and the derivatized carboxyl functionalities result from cross-linking of carbohydrates with a multifunctional carbodiimide described above. In some embodiments, the multifunctional carbodiimide is a biscarbodiimide.

Each Carbohydrate in the preceding formula can be different or the same Carbohydrate molecule, e.g., the cross-link can be an intermolecular or intramolecular cross-link. Each U can be the same or different and is an optionally substituted N-acyl urea or O-acyl isourea. As used herein, the term "at least about 1% by mole cross-linked" means that carbohydrates are cross-linked with each other via derivatized functionalities of the carbohydrates, such as O-acylisoureas or N-acylureas, wherein the derivatized functionalities are at least about 1% by mole of the total functionalities of the individual carbohydrate.

In another embodiment, the N-acylurea or O-acylisourea results from cross-linking with the multifunctional carbodiimide. In further embodiments, a monocarbodiimide may be employed in combination with a multifunctional carbodiimide. Certain suitable examples of monocarbodiimides and multifunctional carbodiimide are described above. Use of a multifunctional carbodiimide to prepare the modified carbohydrate derivative causes cross-linking of the carbohydrate. For example, use of a biscarbodiimide results in a cross-linking between carboxyl groups present in the repeating units of the carbohydrate, since the biscarbodiimide is difunctional. The carboxyl group may be present in the same polymer chain, resulting in an intramolecular cross-linked product, or present on two different polymer chains, resulting in an intermolecular cross-linked product.

The reaction of carbohydrate with a biscarbodiimide rather than a monocarbodiimide does not change the mechanism of reaction, but can cause the product to be cross-linked.

The reaction of carbohydrate with a biscarbodiimide cross-linking reagent, in the presence of an available proton, is believed to comprise protonation in the first step. The acid anion can then attach to the carbon atom of the cation formed, resulting in the formation of an O-acyl isourea intermediate. The acyl group in the intermediate can migrate from the oxygen atom to a nitrogen atom to produce a N-acyl isourea derivative of the carbohydrate. It is believed that the O-to-N migration can be incomplete, resulting in a product reaction mixture that can include both the N-acyl urea and the O-acyl isourea. Thus, a cross-link resulting from reaction of a biscarbodiimide with the uncross-linked carbohydrate precursor typically can contain two O-acyl isoureas connected through $R_2$, as represented in the following structural formula (VI):

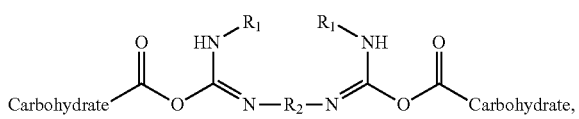

(VI)

or an O-acyl isourea and an N-acyl urea connected through $R_2$, as represented in the following structural formula (VII):

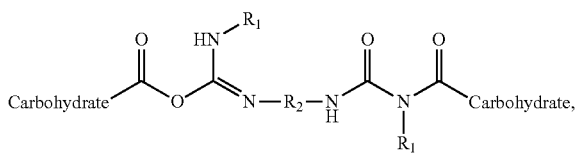

(VII)

or two N-acyl ureas connected through $R_2$, as represented in the following structural formula (VIII):

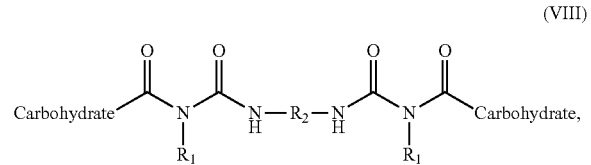
(VIII)

The mixed products can be used separately or together to prepare the injectable compositions according to embodiments of the present disclosure.

The term "hydrocarbyl," as used herein, means a monovalent moiety obtained upon removal of a hydrogen atom from a parent hydrocarbon. As used herein, hydrocarbylene groups are divalent hydrocarbons. Typically, hydrocarbyl and hydrocarbylene groups contain 1-25 carbon atoms, 1-12 carbon atoms or 1-6 carbon atoms. Hydrocarbyl and hydrocarbylene groups can be independently substituted or unsubstituted, cyclic or acyclic, branched or unbranched, and saturated or unsaturated. Optionally, hydrocarbyl and hydrocarbylene groups independently can be interrupted by one or more hetero atoms (e.g., oxygen, sulfur and nitrogen). Examples of hydrocarbyl groups include aliphatic and aryl groups. Substituted hydrocarbyl and hydrocarbylene groups can independently have more than one substituent.

The term "substituent," as used herein, means a chemical group which replaces a hydrogen atom of a molecule. Representative of such groups are halogen (e.g., —F, —Cl, —Br, —I), amino, nitro, cyano, —OH, alkoxy, alkyl, alkenyl, alkynyl, aryl, haloalkoxy, haloalkyl, haloalkenyl, haloalkynyl, alkyl amino, haloalkyl amino, aryl amido, sulfamido, sulfate, sulfonate, phosphate, phosphino, phosphonate, carboxylate, carboxamido, and the like.

An "alkyl" group, as used herein, is a saturated aliphatic group. The alkyl group can be straight chained or branched, or cyclic or acyclic. Typically, an alkyl group has 1-25 carbon atoms. Examples of alkyl groups include methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonodecyl, eicosyl, heneicosyl, docosyl, tricosyl, tetracosyl, pentacosyl, and the isomeric forms thereof. An alkyl group may be substituted with one or more substituents independently selected for each position.

An "alkylene" group, as used herein, is a saturated aliphatic group that is bonded to two other groups each through a single covalent bond. The alkylene group can be straight chained or branched, or cyclic or acyclic. Typically, an alkylene group has 1-25 carbon atoms. Examples of alkylene groups include methylene, ethylene, propylene, butylene, pentylene, hexylene, heptylene, octylene, 1,6-hexamethylene, 1,8-octamethylene, 1,10-decamethylene, 1,12-dodecamethylene and the isomeric forms thereof. An alkylene group may be substituted with one or more substituents independently selected for each position.

As used herein, an "alkenyl" group is an aliphatic group that contains a double bond. Typically, an alkenyl group has 2 to 25 carbon atoms. Examples include vinyl, allyl, butenyl, pentenyl, hexenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, and isomeric forms thereof.

As used herein, an "alkenylene" group is an aliphatic group that contains a double bond. Typically, an alkenylene group has 2 to 25 carbon atoms. Examples include butenylene, pentenylene, hexenylene, octenylene, nonenylene and isomeric forms thereof.

As used herein, an "alkynyl" group is an aliphatic group that contains a triple bond. Typically, an alkynyl group has 2 to 25 carbon atoms. Examples include vinyl, allyl, butynyl, pentynyl, hexynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, heneicosynyl, docosynyl, tricosynyl, tetracosynyl, pentacosynyl, and isomeric forms thereof.

As used herein, an "alkynylene" group is an aliphatic group that contains a triple bond. Typically, an alkynylene group has 2 to 25 carbon atoms. Examples include vinylene, allylene, butynylene, pentynylene, hexynylene, octynylene and isomeric forms thereof.

The term "aryl" as used herein refers to an aromatic ring (including heteroaromatic ring). Particularly, an aryl group that includes one or more heteroatoms is herein referred to "heteroaryl." Examples of aryl groups include phenyl, tolyl, xylyl, naphthyl biphenylyl, triphenylyl, and heteroaryl, such as pyrrolyl, thienyl, furanyl, pyridinyl, oxazolyl, isooxazolyl, thiazolyl, isothiazolyl and quinolinyl. An aryl group may be substituted with one or more substituents independently selected for each position.

The term "arylene" as used herein refers to an aryl ring in a molecule that are bonded to two other groups each through a single covalent bond from two of its ring atoms. Particularly, an arylene group that includes one or more heteroatoms is herein referred to "heteroarylene." Examples of arylene groups include phenylene [—($C_6H_4$)—], such as meta-phenylene and para-phenylene; and heteroarylene groups, such as pyridylene [—($C_5H_3N$)—]; and furanylene [—($C_4H_2O$)—]. An arylene group may be substituted with one or more substituents independently selected for each position.

An alkyl, alkylene, alkenyl, alkenylene group, alkynyl or alkynylene can be optionally substituted with substituted or unsubstituted aryl group to form, for example, an aralkyl group (e.g. benzyl), or aralylene (e.g. —$CH_2$—($C_6H_4$)— or —CH=$CH_2$—($C_6H_4$)—). Similarly, aryl or arylene groups can be optionally substituted with a substituted or unsubstituted alkyl, alkenyl or alkynyl group.

The term "heterocyclyl" refers to a cycloalkyl group wherein one or more ring carbon atoms are replaced with a heteroatom, e.g., aziridyl, azetidyl, pyrrolidyl, piperidyl, thiiranyl, thietanyl, tetrahydrothiophenyl, tetrahydrothiopyranyl, oxiranyl, oxetanyl, tetrahydrofuranyl, tetrahydropyranyl, morpholinyl, and the like.

The term "heterocyclylene" refers to a cycloalkylene group wherein one or more ring carbon atoms are replaced with a heteroatom, e.g., 2,5-tetrahydrofuranylene.

An alkoxy group is an alkyl group connected through an oxygen atom, e.g., methoxy, ethoxy, propoxy and the like.

An aryloxy group is an aryl group connected through an oxygen atom, e.g., phenoxy and the like.

An aralkyloxy group is an aralkyl group connected through an oxygen atom, e.g., benzyl oxy and the like.

In one embodiment, the modified carbohydrate derivative is at least about 1% by mole cross-linked. The cross-linked carbohydrate gel can be water-soluble or substantially water-insoluble.

In some embodiments, the composition has a viscosity greater than that of room temperature saline. In some embodiments, the composition has a viscosity at room temperature of about 10,000 to 1000,000 cSt, more particularly about 30,000 to 90,000 cSt, and in some cases about 50,000 to 70,000 cSt. The carbohydrate composition should have a viscosity sufficient to maintain some period of residence around the site of injection/administration. In some embodiments, the composition has a maximum viscosity such that it can be extruded from a 5 mL syringe through a 25 gauge needle with a force less than or equal to about 12.5 lbs. In some embodiments, the composition has a maximum viscosity such that it can be extruded from a 5 mL syringe through a 25 gauge needle with a force less than or equal to about 10 lbs. In some embodiments, the composition has a maximum viscosity such that it can be extruded from a 5 mL syringe through a 25 gauge needle with a force less than or equal to about 9 lbs. In some embodiments, the composition has a maximum viscosity such that it can be extruded from a 5 mL syringe through a 25 gauge needle with a force less than or equal to about 8 lbs. In some embodiments, the composition has a maximum viscosity such that it can be extruded from a 5 mL syringe through a 25 gauge needle with a force less than or equal to about 7.5 lbs. In some embodiments, the composition has a maximum viscosity such that it can be extruded from a 5 mL syringe through a 25 gauge needle with a force less than or equal to about 7 lbs. In some embodiments, the composition has a maximum viscosity such that it can be extruded from a 5 mL syringe through a 25 gauge needle with a force less than or equal to about 6 lbs. In some embodiments, the composition has a maximum viscosity such that it can be extruded from a 5 mL syringe through a 25 gauge needle with a force less than or equal to about 5 lbs. In some embodiments, the composition has a maximum viscosity such that it can be extruded from a 5 mL syringe through a 25 gauge needle with a force less than or equal to about 4 lbs. In some embodiments, the composition has a maximum viscosity such that it can be extruded from a 5 mL syringe through a 25 gauge needle with a force less than or equal to about 3 lbs. In some embodiments, the composition has a maximum viscosity such that it can be extruded from a 5 mL syringe through a 25 gauge needle with a force less than or equal to about 2 lbs. In some embodiments, the composition has a maximum viscosity such that it can be extruded from a 5 mL syringe through a 25 gauge needle with a force less than or equal to about 1 lbs.

In some embodiments, the carbohydrate is collagen. Collagen is a major protein component of the extracellular matrix of animals. Collagen is assembled into a complex fibrillar organization. The fibrils are assembled into bundles that form the fibers. The fibrils are made of five microfibrils placed in a staggered arrangement. Each microfibril is a collection of collagen rods. Each collagen rod is a right-handed triple-helix, each strand being itself a left-handed helix. Collagen fibrils are strengthened by covalent intra- and intermolecular cross-links which make the tissues of mature animals insoluble in cold water.

In some embodiments, the carbohydrate is denatured collagen. When suitable treatments are used, collagen rods are extracted and solubilized where they keep their conformation as triple-helices. This is denatured collagen and differs from the native form of collagen, but has not undergone sufficient thermal or chemical treatment to break the intramolecular stabilizing covalent bonds found in collagen.

In some embodiments, the carbohydrate is gelatin. When collagen solutions are extensively heated, or when the native collagen containing tissues are subjected to chemical and thermal treatments, the hydrogen and covalent bonds that stabilize the collagen helices are broken, and the molecules adopt a disordered conformation. By breaking these hydrogen bonds, the polar amine and carboxylic acid groups are now available for binding to polar groups from other sources or themselves. This material is gelatin and is water-soluble at 40-45° C. Gelatin can be obtained by the partial hydrolysis of collagen derived from the skin, white connective tissue, or bones of animals. Gelatin may be derived from an acid-treated precursor or an alkali-treated precursor. Gelatin derived from an acid-treated precursor is known as Type A, and gelatin derived from an alkali-treated precursor is known as Type B. The macromolecular structural changes associated with collagen degradation are basically the same for chemical and partial thermal hydrolysis. In the case of thermal and acid-catalyzed degradation, hydrolytic cleavage predominates within individual collagen chains. In alkaline hydrolysis, cleavage of inter- and intramolecular cross-links predominates. In some embodiments, the gelatin has a molecular mass of about 80,000 to about 200,000 Da. In some embodiments, the polydispersity of the molecular mass of the gelatin is between about 1 and about 3. In some embodiments, the polydispersity of the molecular mass of the gelatin is between about 1.1 and about 2.4. In some embodiments, the gelatin is present in the composition at a concentration of between about 0.01 mM and about 10 mM.

In some embodiments, the carbohydrate is a polysaccharide. In some embodiments, the polysaccharide is a sulfated polysaccharide. In some embodiments, the polysaccharide comprises more than about 10 monosaccharide residues joined to each other by glycosidic linkages. In some embodiments, the polysaccharide is selected from the group consisting of glycosaminoglycans and glucosaminoglycans. In some embodiments, the polysaccharide is selected from the group consisting of dextran, heparan, heparin, hyaluronic acid, alginate, agarose, carrageenan, amylopectin, amylose, glycogen, starch, cellulose, chitin, xanthan gum, gellan gum, galactomannan, and chitosan. In some embodiments, the polysaccharide is a sulfated polysaccharide is selected from the group consisting of heparan sulfate, chondroitin sulfate, dextran sulfate, dermatan sulfate, and keratan sulfate. In some embodiments, the polysaccharide has a molecular mass of about 2,000 to about 8,000,000 Da. In further embodiments, the polysaccharide has a molecular mass of about 20,000 to about 3,000,000 Da. In still further embodiments, the polysaccharide has a molecular mass of between about 20,000 Da and about 1,000,000 Da. Cross-linked carboxy polysaccharides are described in U.S. Pat. No. 5,676,964, the entire contents of which are incorporated herein by reference. Percarboxylated polysaccharides and processes for their preparation are described in U.S. Pat. No. 7,683,038, the entire contents of which are incorporated herein by reference.

In some embodiments, the carbohydrate is dextran. In some embodiments, the dextran has a molecular mass of about 300,000 to about 600,000 Da. In some embodiments the polydispersity of the molecular mass of the dextran is between about 1 and about 3. In some embodiments the polydispersity of the molecular mass of the dextran is between about 1.1 and about 2.4. In some embodiments, the dextran is present in the composition at a concentration of between about 0.01 mM and about 10 mM.

In some embodiments, the carbohydrate is dextran sulfate. Dextran sulfate is a glycosaminoglycan-like polyionic derivative of dextran and has been shown to be useful as a biomaterial and drug for treatment of hyperlipidemia. It can be produced by esterification of dextran, a hydrophilic polymer of glucose synthesized by certain strains of bacteria.

In some embodiments, the carbohydrate is the polysaccharide hyaluronic acid. Hyaluronic acid, also referred to as "HA," is a naturally occurring, water soluble polysaccharide comprising disaccharide units of D-glucuronic acid (GlcUA) and N-acetyl-D-glucosamine (GlcNAc), which are alternately linked, forming a linear polymer that is a major component of the extra-cellular matrix and is widely distributed in animal tissues. High molecular mass HA may comprise 100 to 10,000 disaccharide units. HA often occurs naturally as the sodium salt, sodium hyaluronate. HA, sodium hyaluronate, and preparations of either HA or sodium hyaluronate are often referred to as "hyaluronan." Naturally occurring HA generally has a molecular mass range of about between $6 \times 10^4$ to about $1.2 \times 10^7$ Daltons. It has excellent biocompatibility and does not give a foreign body or allergic reaction when implanted or injected into a patient. An aqueous solution of hyaluronan is viscous even at relatively low solute concentrations. Methods of preparing commercially available hyaluronan are well known. Also known are various methods of coupling HA and cross-linking HA to reduce the water solubility and diffusibility of HA, and to increase the viscosity of HA. See, e.g., U.S. Pat. Nos. 5,356,883, 6,013,679, 6,537,979, 6,548,081, 7,125,860, 8,124,120 and 8,323,617, the entire disclosures of which are incorporated herein by reference. Without wishing to be bound by theory, the inventors posit that because HA is a natural component of tendon ground substance, where it functions to exert a lubricating effect protecting the tendon from sheer and compressive forces, injectable compositions of HA of the present disclosure can be useful in the presently disclosed injectable compositions and methods. Because of its lubricating and viscoelastic properties and osmotic potential, HA can reduce biomechanical resistance and promote the physiological repair processes at the osteotendinous junction.

As used herein, the terms "hyaluronic acid," "HA" and "hyaluronan" also refer to any of the other hyaluronate salts, including, but not limited to, sodium hyaluronate, potassium hyaluronate, magnesium hyaluronate, calcium hyaluronate, and ammonium hyaluronate, including HA derived from bacteria or animals (e.g., avian HA), and cross-linked HA. In some embodiments, the carbohydrate comprises a cross-linked hyaluronic acid. In some embodiments, the carbohydrate comprises a hyaluronic ester. A hyaluronic ester is a hyaluronic acid molecule in which at least one carboxylate group of the hyaluronic acid is esterified with an alcohol. Esters of hyaluronic acid are described in U.S. Pat. Nos. 4,851,521, 7,462,606, 8,178,663, and 8,178,499, the entire contents of which are incorporated herein by reference. In some embodiments, the hyaluronic ester is an ester of hyaluronic acid with at least one alcohol selected from the group consisting of aliphatic, aryl-aliphatic, cycloaliphatic, aromatic, cyclic, and heterocyclic alcohols. In some embodiments, the hyaluronic ester has an esterification percentage from about 20 to about 80%. In some embodiments, the remaining non-esterified HA is salified with an organic or an inorganic base. See, e.g., European Patent No. 0 216 453 and U.S. Pat. No. 4,851,521, the contents of which are hereby incorporated by reference in their entireties. In some embodiments, the hyaluronic ester is represented by the formula (IX):

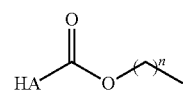

(IX)

wherein HA represents hyaluronic acid and n is an integer between 0 and 20. In some embodiments, the hyaluronic ester is selected from the group consisting of Hyaff7

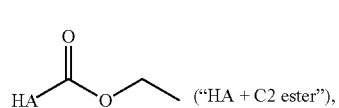
("HA + C2 ester"),

Hyaff11

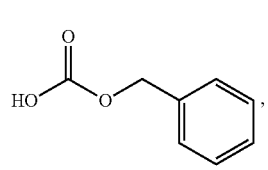

Hyaff73

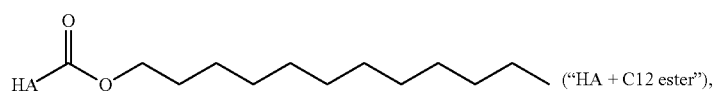
("HA + C12 ester"),

Hyaff91

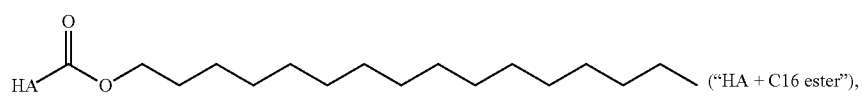
("HA + C16 ester"),

Hyaff92

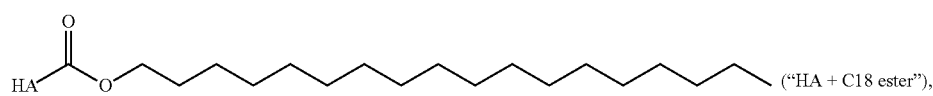
("HA + C18 ester"),

Hyaff107

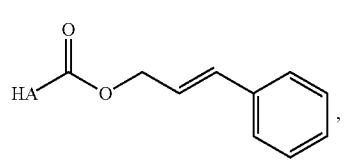

Hyaff120

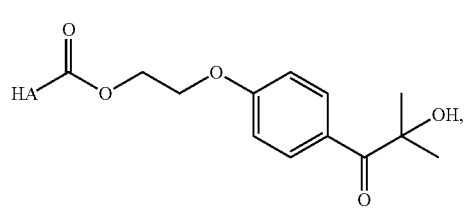

Hyaff302 (Hyaff11/P75+25% C16 ester), Hyaff303 (Hyaff11/P75+25% C18 ester), and Hyaff304 (Hyaff11/P75+25% C20 ester). (P75 indicates 75% esterification). In some embodiments, the hyaluronic ester is selected from the group of hyaluronic esters disclosed in Table 2:

| Name | Description/Structure |
|---|---|
| HYAFF 2 | $C_{15}H_{23}O_{11}N$ |
| HYAFF 5 | $C_{14}H_{20}O_{11}NLi$ |
| HYAFF 7 | $C_{16}H_{25}O_{11}N$ |
| HYAFF 8 | $C_{17}H_{27}O_{11}N$(iso-propyl) |
| HYAFF 9 | $C_{17}H_{27}O_{11}N$(n-propyl) |
| HYAFF 10 | HA + n-butylic ester |
| HYAFF 11 | $C_{21}H_{27}O_{11}N$ |
| HYAFF 12 | HA + cyclohexylic ester |
| HYAFF 13 | $C_{18}H_{29}O_{11}N$ |
| HYAFF 16 | HA + cyclopentylic ester |
| HYAFF 17 | $C_{22}H_{37}O_{11}N$ |
| HYAFF 18 | $C_{25}H_{35}O_{11}N$ |
| HYAFF 19 | $C_{21}H_{35}O_{11}N$ |
| HYAFF 20 | $C_{22}H_{29}O_{11}N$ |
| HYAFF 21 | $C_{19}H_{31}O_{11}N$ |
| HYAFF 22 | $C_{19}H_{31}O_{11}N$(iso) |
| HYAFF 23 | $C_{27}H_{31}O_{11}N$ |
| HYAFF 26 | $C_{22}H_{29}O_{11}N$(ester with 1-phenylethyl alcohol) |
| HYAFF 27 | $C_{16}H_{24}O_{12}N_2$ |
| HYAFF 28 | $C_{22}H_{29}O_{11}N$(ester with 3-methylbenzyl alcohol) |
| HYAFF 29 | $C_{21}H_{25}O_{11}NCl_2$ |
| HYAFF 50 | $C_{18}H_{27}O_{13}N$ |
| HYAFF 51 | $C_{22}H_{26}O_{11}N_2$ |
| HYAFF 52 | $C_{25}H_{35}O_{11}N$ |
| HYAFF 53 | $C_{21}H_{25}O_{11}NF_5$ |
| HYAFF 54 | $C_{24}H_{33}O_{14}N$ |
| HYAFF 55 | $C_{21}H_{26}O_{11}NBr$ |
| HYAFF 56 | $C_{19}H_{31}O_{11}N$ |
| HYAFF 57 | $C_{23}H_{29}O_{11}N$ |
| HYAFF 58 | $C_{21}H_{26}O_{11}NF$ |
| HYAFF 59 | $C_{22}H_{26}O_{11}NF_3$ |
| HYAFF 60 | $C_{21}H_{26}O_{11}NBr$ |
| HYAFF 61 | $C_{21}H_{26}O_{11}NF$(ortho) |
| HYAFF 62 | $C_{21}H_{26}O_{11}NF$(meta) |
| HYAFF 63 | $C_{22}H_{29}O_{11}NF$(para) |
| HYAFF 64 | $C_{22}H_{29}O_{11}NF$(ortho) |
| HYAFF 65 | $C_{21}H_{26}O_{11}NCl$(meta) |
| HYAFF 66 | $C_{21}H_{26}O_{11}NCl$(para) |
| HYAFF 67 | $C_{21}H_{26}O_{11}NCl$(ortho) |
| HYAFF 68 | $C_{21}H_{26}O_{13}NBr$ |
| HYAFF 69 | $C_{21}H_{26}O_{11}NBr$ |
| HYAFF 70 | $C_{23}H_{31}O_{11}N$ |
| HYAFF 71 | $C_{24}H_{41}O_{11}N$ |
| HYAFF 72 | $C_{23}H_{39}O_{11}N$ |
| HYAFF 73 | $C_{25}H_{43}O_{11}N$ |
| HYAFF 74 | $C_{21}H_{25}O_{11}NFCl$ |
| HYAFF 75 | $C_{21}H_{25}O_{11}NCl_2$ |
| HYAFF 76 | $C_{26}H_{37}O_{11}N$ |
| HYAFF 77 | $C_{21}H_{25}O_{11}NF_2$(2,3-difluoro) |
| HYAFF 78 | $C_{21}H_{25}O_{11}NF_2$(2,4-difluoro) |
| HYAFF 79 | $C_{21}H_{25}O_{11}NF_2$(2,5-difluoro) |
| HYAFF 80 | $C_{23}H_{25}O_{11}NF_6$ |
| HYAFF 81 | $C_{21}H_{25}O_{11}NF_2$(2,6-difluoro) |
| HYAFF 82 | $C_{21}H_{25}O_{11}NF_2$(3,4-difluoro) |
| HYAFF 83 | $C_{23}H_{31}O_{11}N$ |
| HYAFF 84 | $C_{23}H_{31}O_{11}NF_6$ |
| HYAFF 86 | HA + pentadecylic ester |
| HYAFF 87 | HA + heptadecylic ester |
| HYAFF 88 | HA + tridecylic ester |
| HYAFF 89 | HA + tetradecylic ester |
| HYAFF 90 | HA + hexylic ester |
| HYAFF 91 | HA + hexadecylic ester |
| HYAFF 92 | HA + octadecylic ester |
| HYAFF 93 | $C_{21}H_{35}O_{11}N$ |
| HYAFF 94 | $C_{23}H_{39}O_{15}N$ |
| HYAFF 95 | $C_{24}H_{41}O_{11}N$ |
| HYAFF 96 | $C_{27}H_{47}O_{11}N$ |
| HYAFF 100 | $C_{22}H_{37}O_{11}N$ |
| HYAFF 101 | $C_{21}H_{35}O_{11}N$ |

In some embodiments, the carbohydrate comprises a hyaluronic amide. A hyaluronic amide is a hyaluronic acid molecule in which at least one carboxylate group of the hyaluronic acid is amidated with an amine. Amides of hyaluronic acid are described in U.S. Pat. No. 7,884,087, the entire contents of which are incorporated herein by reference. In some embodiments, the hyaluronic amide is an amide of hyaluronic acid with at least one amide selected from the group consisting of aliphatic, aryl-aliphatic, cycloaliphatic, aromatic, cyclic, and heterocyclic amines. In some embodiments, the hyaluronic amide has an amidation percentage from about 0.1 to about 50%. In some embodiments, the remaining non-amidated HA is salified with an organic or an inorganic base. See European Patent No. 1 095 064, the contents of which are hereby incorporated by reference in their entirety. In some embodiments, the hyaluronic amide is represented by the formula (X):

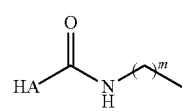

(X)

wherein HA represents hyaluronic acid and m is an integer between 0 and 20. In some embodiments, the hyaluronic amide is selected from the group consisting of Hyadd1 ("HA+benzylamino amide"), Hyadd2

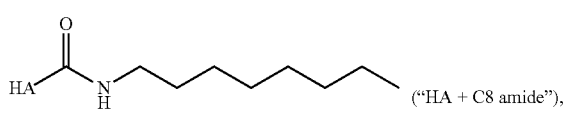

("HA + C8 amide"),

Hyadd3

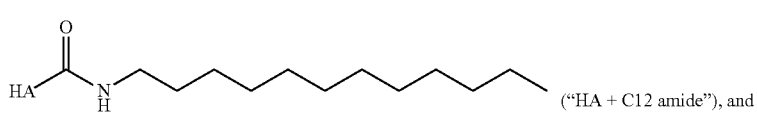

("HA + C12 amide"), and

Hyadd4

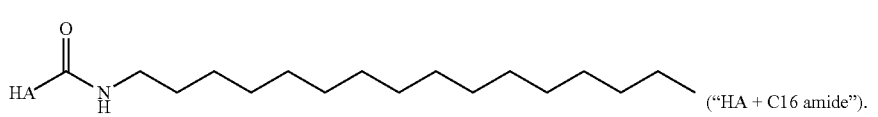

("HA + C16 amide").

In some embodiments, the carbohydrate is a sulfated hyaluronic acid or an ester or amide thereof. Sulfated hyaluronic acids and esters thereof are described in U.S. Pat. No. 6,027,741, the entire contents of which are incorporated herein by reference. Biomaterials comprising N-sulfated hyaluronic acid compounds or derivatives thereof are described in U.S. Pat. No. 6,579,978, the entire contents of which are incorporated herein by reference.

The carbohydrates disclosed herein can be formed as hydrogels, gel particles or micelles. As the term is used herein, a "hydrogel" is a cross-linked macromolecular network that can swell in water or biological fluids, and can retain a significant portion of water within its structure without dissolving. Administration of the carbohydrates formed as hydrogels results in an increase in osmotic potential, thereby drawing water into the area around the injection site. As used herein, the term "swelling" refers to the taking up of a liquid, for example water, by a gel with an increase in volume, typically with the addition of heat and pressure. Methods of preparing cross-linked bioactive hydrogel matrices are known, for example in U.S. Pat. No. 8,053,423, the entire contents of which are incorporated here by reference. Ester derivatives of hyaluronic acid for the preparation of hydrogel materials by photocuring are described in U.S. Pat. No. 7,462,606, the entire contents of which are incorporated herein by reference. As used herein, the term "micelle" refers to a molecular assembly in which amphiphilic molecules are arranged in a spherical structure such that all the hydrophobic portions of the molecules are directed inward, leaving the hydrophilic portions in contact with the surrounding aqueous phase. As used here, the term "reverse micelle" refers to a molecular assembly in which amphiphilic molecules are arranges in a spherical structure such that all the hydrophilic portions of the molecules are directed inward, leaving the hydrophobic portions in contact with the surrounding solvent phase.

In some embodiments, the carbohydrates disclosed herein are metabolically cleared and/or are unstable in the physiological medium into which they are injected. In some embodiments, the carbohydrate has a clearance or stability half-life of about 3 days to about 60 days once injected. In further embodiments, the carbohydrate has a clearance or stability half-life of about 45 days once injected. In further embodiments, the carbohydrate has a clearance or stability half-life of about 30 days once injected. In further embodiments, the carbohydrate has a clearance or stability half-life of about 25 days once injected. In further embodiments, the carbohydrate has a clearance or stability half-life of about 20 days once injected. In further embodiments, the carbohydrate has a clearance or stability half-life of about 15 days once injected. In further embodiments, the carbohydrate has a clearance or stability half-life of about 14 days once injected. In further embodiments, the carbohydrate has a clearance or stability half-life of about 7 days once injected. In further embodiments, the carbohydrate has a clearance or stability half-life of about 5 days once injected. In further embodiments, the carbohydrate has a clearance or stability half-life of about 3 days once injected.

Pharmaceutical Compositions

The present disclosure also relates to pharmaceutical compositions comprising a carbohydrate disclosed herein. Routes of administration and dosages of effective amounts of the pharmaceutical compositions are also disclosed. The injectable compositions disclosed herein can be administered in combination with other pharmaceutical agents in a variety of protocols for effective treatment of a condition indicated herein.

The injectable compositions disclosed herein are administered as disclosed herein. The dosage administered will be dependent upon the age and health of the recipient, kind of concurrent treatment, if any, frequency of treatment, and the nature of the effect desired.

In addition to the components disclosed herein, the injectable compositions disclosed herein may further comprise at least one of any suitable auxiliaries including, but not limited to, diluents, binders, stabilizers, buffers, salts, lipophilic solvents, preservatives, adjuvants or the like. Pharmaceutically acceptable auxiliaries are preferred. Examples and methods of preparing such sterile solutions are well known in the art and can be found in well-known texts such as, but not limited to, Remington's Pharmaceutical Sciences, Martin, E. W., ed., Mack Publishing Company, 19th ed. (1995). Pharmaceutically acceptable carriers can be routinely selected that are suitable for the mode of administration, solubility and/or stability of the injectable composition.

Pharmaceutical excipients and additives useful in the injectable compositions disclosed herein can also include, but are not limited to, proteins, peptides, amino acids, lipids, and additional carbohydrates (e.g., sugars, including monosaccharides, di-, tri-, tetra-, and oligosaccharides; derivatized sugars such as alditols, aldonic acids, esterified sugars and the like; and polysaccharides or sugar polymers), which can be present singly or in combination, comprising alone or in combination in ranges of 0.01-99.99% by weight or volume. Exemplary protein excipients include serum albumin such as human serum albumin (HSA), recombinant human albumin (rHA), gelatin, casein, and the like. Representative amino acid components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. Other buffering agents that can be useful in the injectable compositions disclosed herein include EDTA.

In some embodiments, the injectable compositions of the present disclosure can further include an additional agent. In some embodiments, the additional agent is a small molecule. In some embodiments, the small molecule is a protease agonist. In some embodiments, the small molecule is an anti-inflammatory agent. In some embodiments, the additional agent is selected from the group consisting of growth and/or differentiation factors and/or hormones (e.g., BMPs, GDFs, interleukins, prostaglandins, thromboxanes, leukotrienes and cytokines), antibiotics (e.g., penicillin, streptomycin and linocomycin), antifungals, analgesics, anesthetics, steroidal and non-steroidal anti-inflammatory agents, chondroregenerative agents, chondroprotective agents, matrix metalloproteinase (MMP) inhibitors, tissue inhibitors of matrix metalloproteinase (TIMPs), bone protective agents, bone regenerating agents, bone anabolic agents, bone resorption inhibitors, and bone osteoclast inhibiting agents, any synthetic analogues and pharmaceutically-active fragments thereof, and combinations thereof. In some embodiments, the additional agent is selected from the group consisting of sorbitol, mannitol, an antioxidant (e.g., epigallocatechin gallate, resveratrol, curcumin), IGF-1, PDGF, VEGF, alpha-2-macroglobulin, and combinations thereof. In some embodiments, the additional agent is a cell. In further embodiments, the additional agent is a cell selected from the group consisting of stem cells, somatic cells, platelet-rich plasma, platelet-poor plasma and combinations thereof. In some embodiments, the additional agent is a sterol, stanol or derivative thereof. In some embodiments, the additional agent is selected from the group consisting of cholesterol, stigmasterol, stigmastanol, phytosterol, sitosterol, β-sitosterol, ergosterol, campesterol, brassicasterol, thiocholesterol, and mixtures thereof. In further embodiments, the additional agent is a triterpene alcohol or derivative thereof. In some embodiments, the additional agent is selected from the group consisting of lupeol, cycloartenol, and mixtures thereof.

DETAILED DESCRIPTION OF THE DRAWINGS

FIG. 1 shows a schematic of an exemplary embodiment of a peri-osteotendinous or intra-osteotendinous injection of a composition as disclosed herein for the treatment of an elbow tendinopathy. A syringe 107 containing a composition 108 as disclosed herein is injected into the injection site 105, which is disposed at the osteotendinous junction 104, which is the location where the degenerate tendon 102 meets the bone 101 (in this case, the lateral epicondyle 110). The osteotendinous junction 104 is distal from the musculotendinous junction 109, which is where the healthy tendon 102 meets muscle 103. The needle 106 is inserted into the injection site 105, and force is applied to syringe 107 to expel the composition 108 through the needle 106 and into the tendon at the osteotendinous junction 104 (i.e., intra-osteotendinously) or into the space around the osteotendinous junction 104 (i.e., peri-osteotendinously).

Figure 2:
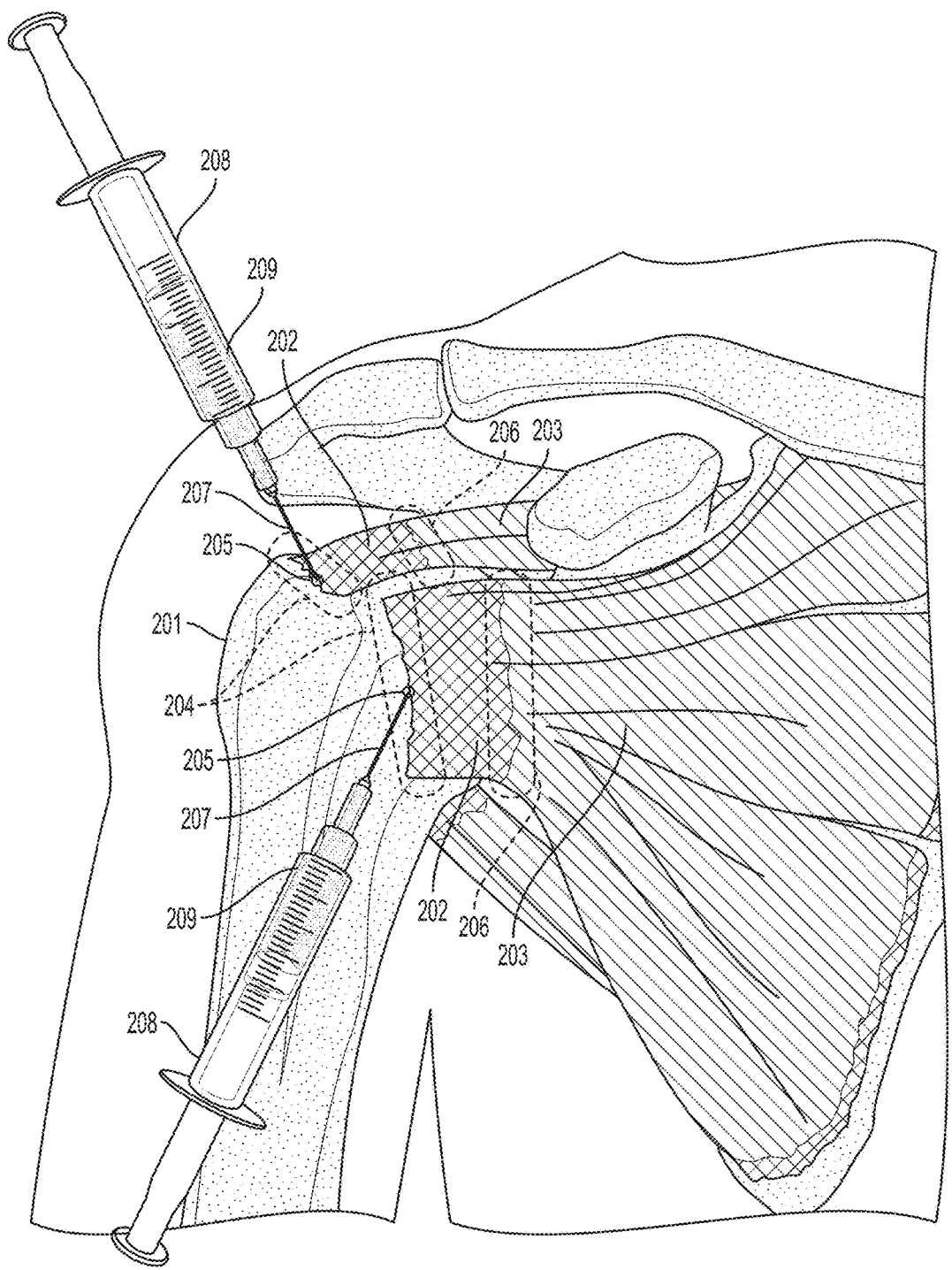
FIG. 2 shows a schematic of exemplary embodiments of peri-osteotendinous or intra-osteotendinous injection of a composition as disclosed herein for the treatment of a rotator cuff tendinopathy.

FIG. 2 shows a schematic of exemplary embodiments of peri-osteotendinous or intra-osteotendinous injection of a composition as disclosed herein for the treatment of a rotator cuff tendinopathy. Syringes 208 containing compositions 209 as disclosed herein are injected into the injection sites 205, which are disposed at osteotendinous junctions 204, which is the location where the degenerate tendons 202 meet the bone 201. The osteotendinous junctions 204 are distal from the musculotendinous junctions 206, which are where the healthy tendons 202 meet muscle 203. The needles 207 are inserted into the injection sites 205, and force is applied to syringes 208 to expel the compositions 209 through the needles 207 and into the tendon at the osteotendinous junctions 204 (i.e., intra-osteotendinously) or into the space around the osteotendinous junctions 204 (i.e., peri-osteotendinously).

EXAMPLES

The following examples further describe and demonstrate embodiments within the scope of the present disclosure. The examples are given solely for the purpose of illustration and are not to be construed as limitations of the present disclosure, as many variations thereof are possible without departing from the spirit and scope of the disclosure.

Example 1: Clinical Identification of Tendon Injury

This example provides an exemplary method for assessing for tendon injury that can be treated with the compositions and methods disclosed herein. Patients assess pain on a VAS at rest and after assessment of grip strength, as determined using a jamar hydraulic hand dynamometer (Sammons Preston, Bolingbrook, Ill.). Assessment is conducted with the patient's elbow fully extended, shoulder in neutral position and the dynamometer's handle in the middle position. Patients perform three grip tests on the affected arm with a mean score calculated and used for analysis.

Alternatively, or in addition, physicians use a disabilities of the arm, shoulder, and hand ("DASH") questionnaire to identify tendon injury. The patient is asked to complete a questionnaire ranking various activities (e.g., open a tight jar, write, or turn a key) on a scale of 1 through 5, where 1 is no difficulty, 2 is mild difficulty, 3 is moderate difficulty, 4 is severe difficulty, and 5 is unable. The DASH score is calculated by the formula:

$$DASH\ Score = \frac{\sum(n\ responses) - 1}{n} \times 25$$

where n is equal to the number of completed responses. A DASH score may not be calculated if there are greater than three missing responses on the questionnaire.

Alternatively, or in addition, physicians use a patient-related tennis elbow evaluation ("PRTEE") questionnaire to identify tendon injury. The patient is asked to complete a questionnaire ranking various activities (e.g., pain at rest, turning a key, or performing household work) on a scale of 1 through 10, where 1 is no pain and/or difficulty performing a task and 10 is the worst imaginable pain or the inability to perform a task. Activities may be divided into pain scores and function scores. Non-responses are minimized by confirming with the patient that if they could not complete the task it should be recorded as a 10, and encouraging them to estimate average difficulty. If the patient never performs an activity, it should be left blank. Pain subscale, function subscale and total score are reported.

Example 2: Methods of Testing Carbohydrate Biomechanical Efficacy In Vitro

This example provides an exemplary method of in vitro testing to evaluate the biomechanical efficacy of a carbohydrate that can be used in connection with the compositions and methods disclosed herein. The biomechanical properties of porcine tendons are evaluated following soaking for 30 minutes in carbohydrate, or injection of saline or carbohydrate into the tendon. Injections occurred at the area of maximum biomechanical strain to mimic injection at the osteotendinous junction in patients in need thereof. The test group that was bathed in sodium hyaluronic solution was used to mimic "flow" of excess solution from sites distal to the area of maximum biomechanical strains, including the musculotendinous junction. The mechanical properties under a tensile loading profile are examined. Time zero histology is performed for each group to document and examine the effect of the treatment based on routine paraffin histology. This portion of the study also examines the effect of saline or carbohydrate on swelling of the tendon based on weights.

TABLE 3

| Biomechanical Testing of Porcine Tendons | | |
|---|---|---|
| Group # | Treatment | Stress relaxation |
| 1 | Saline Injection | 1 displacement (2 mm) and n = 6 |
| 2 | Carbohydrate Soaking | 1 displacement (2 mm) and n = 6 |
| 3 | Carbohydrate Injection | 1 displacement (2 mm) and n = 6 |

Figure 3:
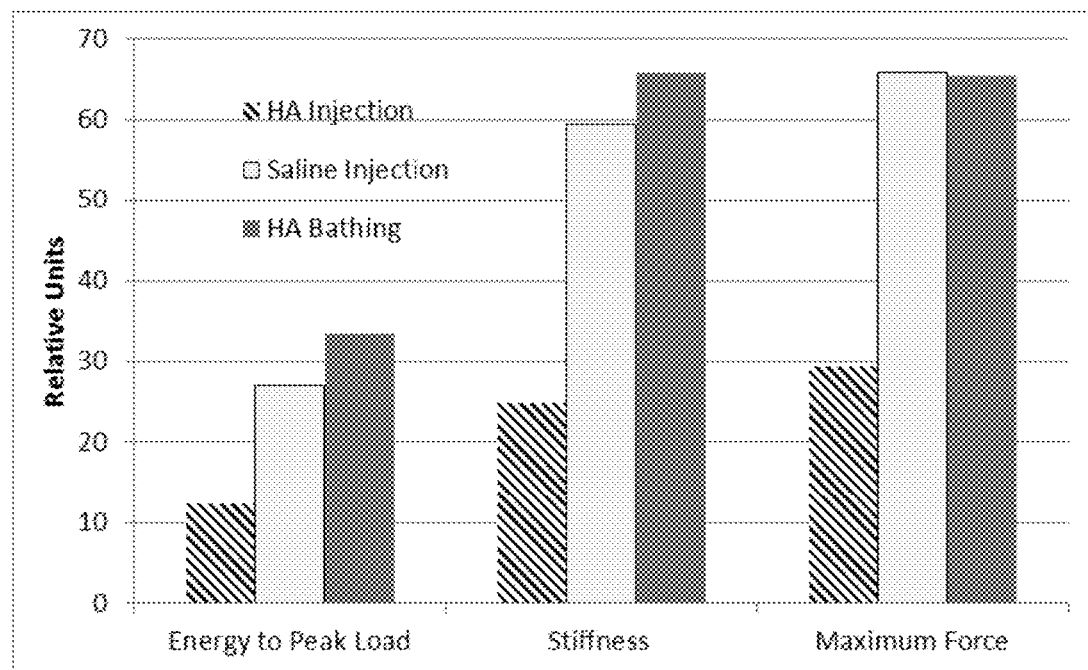
FIG. 3 provides a bar chart showing improved tendon biomechanics associated with injection of sodium hyaluronate compared to saline injection or sodium hyaluronate bathing.

Mechanical testing is performed using a calibrated servohydraulic testing machine. The experimental design evaluates the in vitro mechanical properties of the tendons in stress relaxation. Two displacement levels are performed as outlined in Table 3. The stress relaxation studies are performed for 300 seconds and the data analyzed for differences in relaxation, including mean energy to peak load and mean stiffness. The results show that carbohydrate injection results in a significant reduction in energy to peak load, stiffness, and maximum force for stress relaxation relative to injection of saline or soaking in carbohydrate. See FIG. 3. The results further show that carbohydrate injection is superior to saline in soaking experiments.

Figure 4:
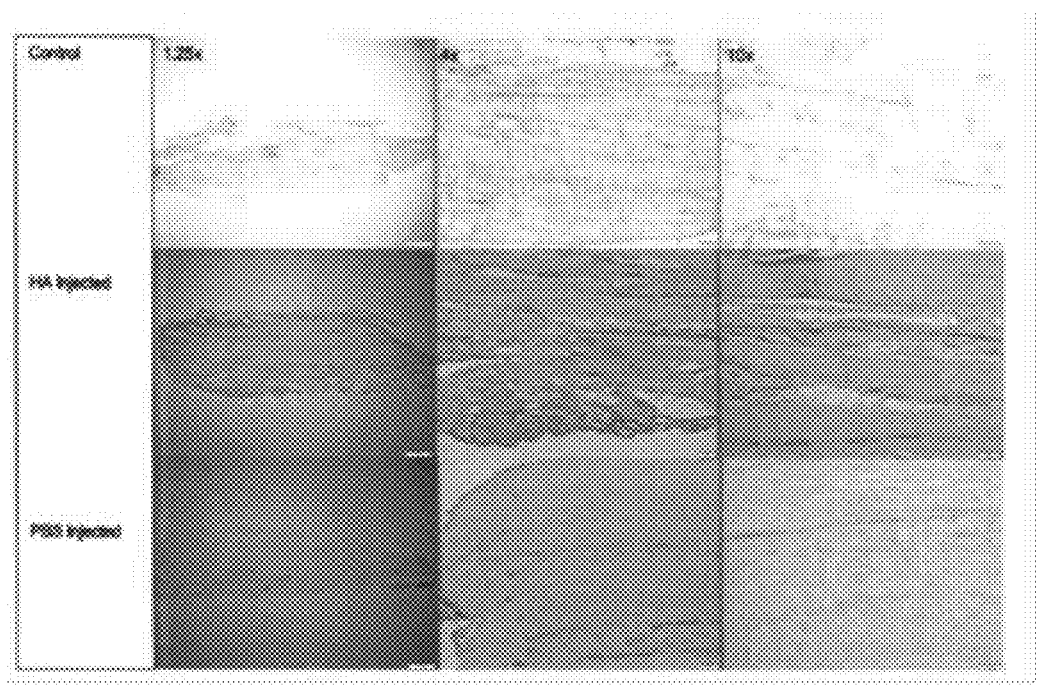
FIG. 4 shows histological staining (H&E) of porcine tendons following injection of hyaluronic acid or saline.

Two tendons from each group are processed for time 0 histology to determine if the treatment conditions have altered the tendon at the histological level. After fixation, the tendons are processed for paraffin histology. The units are placed into embedding blocks for paraffin processing. Each paraffin block is sectioned (5 microns) using a Leica Microtome and placed on slides for haematoxylin and eosin (H&E), picrosirius red and tetrachrome staining. Stained sections are examined under light microscopy using an Olympus Microscope with an Olympus DP72 high resolution video camera to capture images. The reviewer is blinded to time points and treatment groups. Histology is qualitatively assessed for each group and a summary is written. Representative images at low and high power of each slide are taken. The stained slides are reviewed under low magnification to provide an overview of the section for documentation purpose using a 1.25× objective (scale bar=1 mm). The sections are carefully examined at higher magnification (4× objective, scale bar=200 microns) as well as under high power fields (10× objective, scale bar=100 microns, 20× objective, scale bar=50 microns, 40× objective, scale bar=20 microns). Two tendons from each group are also examined for hydration based on wet and dry weight. The results show that at the ultrastructural level, injection of carbohydrate results in separation of the tendon at the fascicle level due to the viscosity of the composition. (See FIG. 4, where lighter areas indicate areas of fascicle separation).

Example 3: Method of Testing Carbohydrate Biochemical Efficacy In Vitro

This example provides an exemplary in vitro method to evaluate the efficacy of a carbohydrate that can be used in connection with the compositions and methods disclosed herein.

Figure 5:
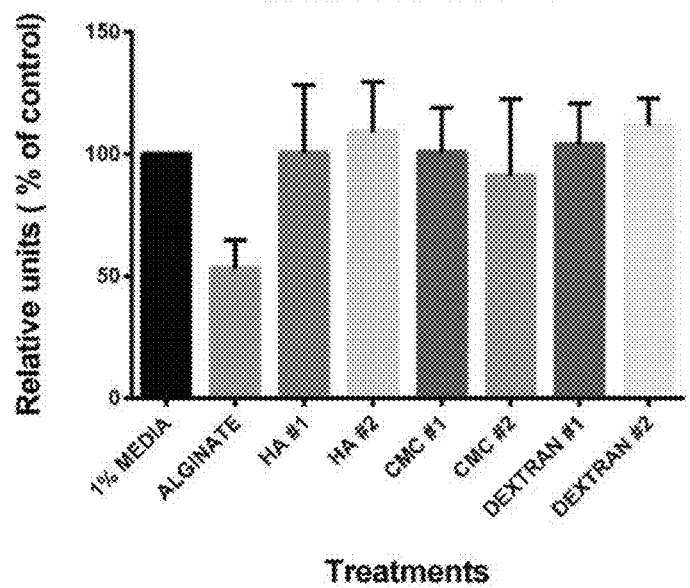
FIG. 5 provides a bar chart showing tenocyte proliferation for tenocytes treated with various carbohydrates.
Figure 5:
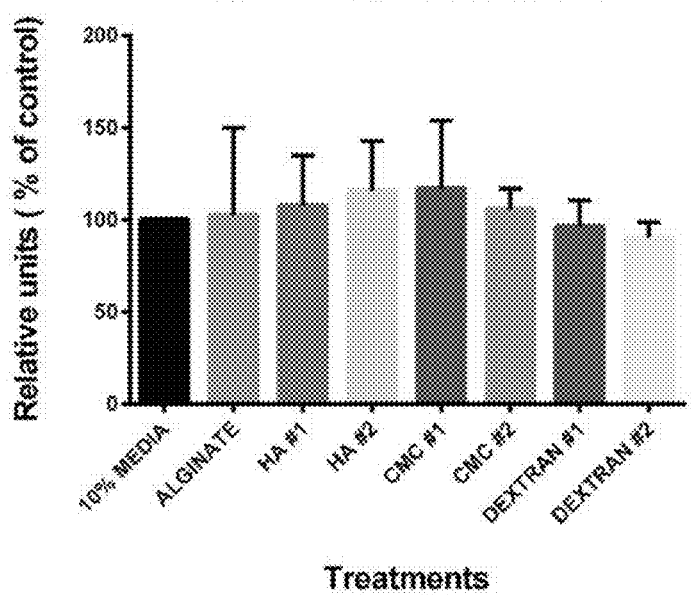
Figure 6:
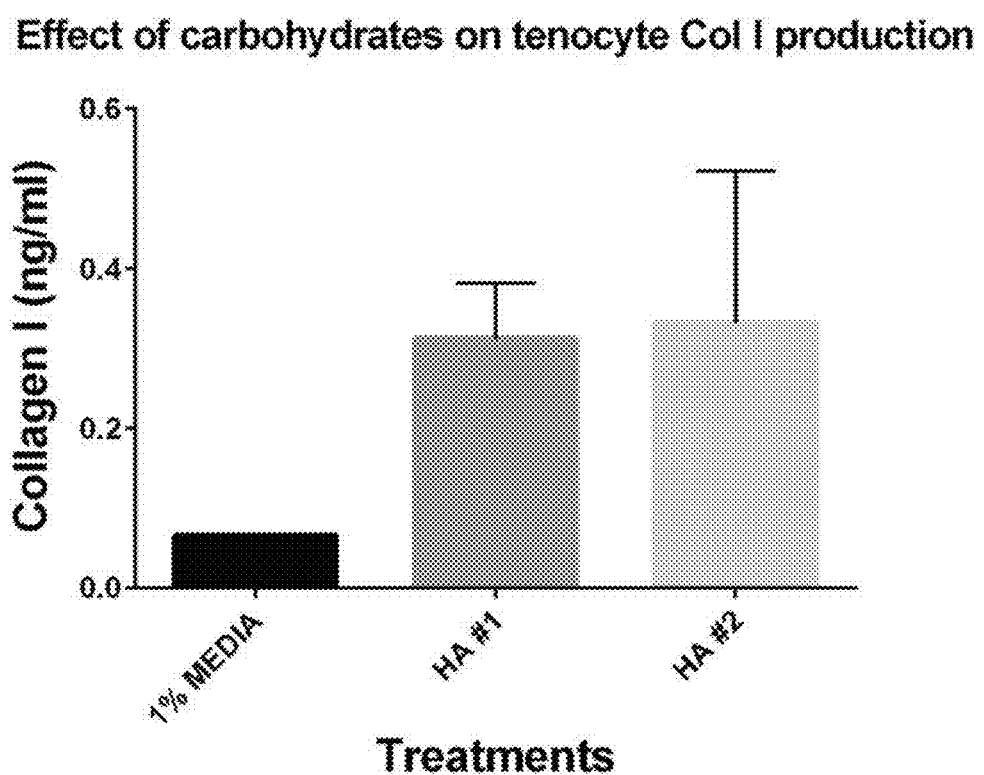
FIG. 6 provides a bar chart showing the effect of carbohydrates on tenocyte collagen I production.
Figure 7:
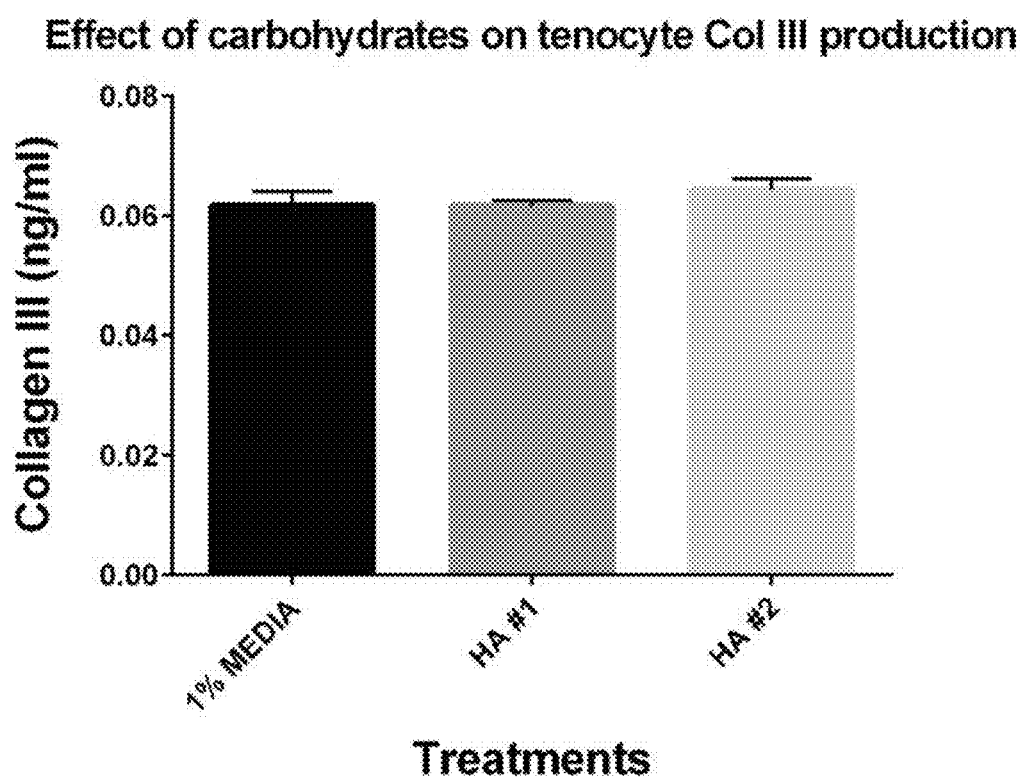
FIG. 7 provides a bar chart showing the effect of carbohydrates on tenocyte collagen III production.

To evaluate the effect of hyaluronic acid (HA) on tenocyte biology, tenocytes (Zen-Bio, RTP, NC) are plated at a density of $1 \times 10^5$ cells per $cm^2$ in 6 well rat collagen type I plates (VWR, Radnor, Pa.) containing tenocyte media (Zen-Bio, RTP, NC) supplemented with low (1%) or normal (10%) levels of serum. Tenocytes are treated with various carbohydrates including dextran, carboxymethylcellulose, hyaluronic acid and alginate to assess their effects on tenocyte proliferation (FIG. 5). All carbohydrates are prepared by mixing with tenocyte media on a rotator overnight at room temperature. Proliferation is assessed using Cell Titer Glo assay kits (Promega, Madison, Wis.). Tenocytes are also treated with hyaluronic acid (HA #1 and HA #2) to determine their effects on collagen I and III production using human Col I (Chondrex, Redmond, Wash.) and human Col III (MyBioSource, San Diego, Calif.) ELISA assay kits. The results indicate that HA #1 and HA #2 stimulate collagen I production vs media control alone (see FIG. 6), however, no effect was seen on collagen III production (see FIG. 7). The carbohydrates had no proliferative effect on tenocytes over media control alone (see FIG. 5).

Example 4: Method of Treating Tendinopathy

This example provides an exemplary method for the treatment of tendinopathy as disclosed herein. A patient in need of treatment is injected either peri-osteotendinously or intra-osteotendinously with a carbohydrate. The injection occurs specifically at the tendon-bone interface (i.e., the osteotendinous junction), and distal from the musculotendinous junction. The injection is administered using a fanning or peppering technique. Once the injection is complete, the limb is rotated medially and laterally five times, and flexed and extended five times. The patients pain and function is reduced and restored, respectively, using clinical measures (e.g., VAS, DASH, PRTEE, etc.). VAS scores at rest and during grip show an improvement by at least one unit 30 days post-injection. DASH scores show an improvement by at least one unit 30 days post-injection. PRTEE scores show an improvement by at least one unit 30 days post-injection. Treatment consists of weekly injections followed by post-injection flexion, extension and medial and lateral rotation for up to six months. Treatment does not involve the use of a structural brace, whether internally or externally, and instead facilitates movement of the injured limb.

As will be apparent to one of ordinary skill in the art from a reading of this disclosure, the present disclosure can be embodied in forms other than those specifically disclosed above. The particular embodiments described above are, therefore, to be considered as illustrative and not restrictive. Those skilled in the art will recognize, or be able to ascertain, using no more than routine experimentation, numerous equivalents to the specific embodiments described herein. The scope of the disclosure is as set forth in the appended claims and equivalents thereof, rather than being limited to the examples contained in the foregoing description. The contents of all of the references disclosed herein are incorporated by reference in their entirety.

What is claimed is:

1. A method for stabilizing, ameliorating, or remedying an injured tendon in an animal or a human in need thereof, the method comprising administering an injectable composition comprising a carbohydrate to the animal or the human, wherein
   said composition comprises an effective amount of carbohydrate to increase tendon hydration and lubrication at the osteotendinous junction;
   said composition is administered via intra-osteotendinous injection at zone one, zone two, zone three, or zone four of the osteotendinous junction; and
   wherein said carbohydrate comprises hyaluronic acid, or an ester, acylurea, acyl isourea, disulfide, or amide thereof.

2. The method of claim 1, wherein said carbohydrate contains at least one functional group selected from the group consisting of thiols, alcohols, amines, carboxyl groups, aldehydes, amides, esters, ketones, and combinations thereof.

3. The method of claim 1, wherein said carbohydrate has a molecular mass of about 1,000,000 to about 3,000,000 Daltons.

4. The method of claim 1, wherein said carbohydrate is not cross-linked.

5. The method of claim 1, wherein said carbohydrate comprises at least one cross-link.

6. The method of claim 1, wherein said carbohydrate is present in said composition at a concentration of about 5-30 mg/mL.

7. The method of claim 1, wherein the composition further comprises a recombinant protein.

8. The method of claim 1, wherein the composition further comprises a small molecule.

9. The method of claim 1, wherein the composition further comprises a somatic cell, platelet rich plasma (PRP), platelet poor plasma (PPP), stem cell allografts, stem cell autografts, bone marrow aspirate (BMA), bone marrow aspirate concentrate (BMAC), autologous fibroblast, or autologous myoblasts.

10. The composition of claim 1, wherein said carbohydrate further comprises collagen, gelatin, a polysaccharide, or combinations thereof.

11. The method of claim 10, wherein said carbohydrate further comprises a polysaccharide.

12. The method of claim 11, wherein said polysaccharide is selected from the group consisting of dextran, heparan, heparin, alginate, agarose, carrageenan, amylopectin, amylose, glycogen, starch, cellulose, chondroitin, dermatan, keratan, chitin, chitosan, carboxymethyl cellulose ("CMC"), xanthan gum, gellan gum, galactomannan, and combinations thereof.

13. The method of claim 1, wherein said hyaluronic acid is selected from the group consisting of hyaluronan, sodium hyaluronate, potassium hyaluronate, magnesium hyaluronate, calcium hyaluronate, ammonium hyaluronate, and combinations thereof.

14. The method of claim 13, wherein said hyaluronic acid comprises a hyaluronic ester.

15. The method of claim 13, wherein said hyaluronic acid comprises a hyaluronic amide.

16. The method of claim 1, wherein said osteotendinous junction exhibits at least one degenerative characteristic selected from the group consisting of (i) an increase in Collagen III relative to normal tendon, (ii) a decrease in Collagen I relative to normal tendon, (iii) an increased observation of micro-tearing relative to normal tendon, (iv) an increase in disorganization of collagen micro-network relative to normal tendon, (v) an increase in fibroblastic infiltration relative to normal tendon, (vi) an increase in cell rounding relative to normal tendon, (vii) an increase in angiogenesis relative to normal tendon, (viii) an increase in cellularity relative to normal tendon, (ix) an increase in tendon gliding resistance relative to normal tendon, and (x) a dull gray appearance relative to normal tendon.

17. The method of claim 1, wherein administration of the composition biomechanically reduces biomechanical interference.

18. The method of claim 1, wherein said composition is injected at a site distal from the musculotendinous junction.

19. The method of claim 1, wherein the composition is not administered via peri-musculotendinous or intra-musculotendinous injection.

20. The method of claim 1, wherein said method comprises a plurality of injections of said composition at different times.

21. The method of claim 20, wherein the method comprises a first injection of said composition and a second injection of said composition, wherein the second injection is administered five to ten days after the first injection.

22. The method of claim 1, wherein the method further comprises post-injection joint manipulation or massage immediately following injection, or one week to six months post-injection, or one week to five months post-injection, or one week to four months post-injection.

23. The method of claim 1, wherein the injured tendon exhibits increased pain compared to the tendon of a non-affected patient.

24. The method of claim 23, wherein the increased pain is assessed using a scale selected from the group consisting of Visual Analog Scale (VAS), Disabilities of the Arm, Shoulder, and Hand (DASH), and Patient-Related Tennis Elbow Evaluation (PRTEE).

* * * * *